US012599310B2

(12) United States Patent
Verkruijsse et al.

(10) Patent No.: US 12,599,310 B2
(45) Date of Patent: Apr. 14, 2026

(54) DEVICE, METHOD AND SYSTEMS FOR PROVIDING IMAGING OF ONE OR MORE ASPECTS OF BLOOD PERFUSION

(71) Applicant: KONINKLIJKE PHILIPS N.V., Eindhoven (NL)

(72) Inventors: Willem Verkruijsse, Veldhoven (NL); Mark Josephus Henricus van Gastel, Tilburg (NL); Age Jochem van Dalfsen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 229 days.

(21) Appl. No.: 18/267,932

(22) PCT Filed: Dec. 7, 2021

(86) PCT No.: PCT/EP2021/084611
§ 371 (c)(1),
(2) Date: Jun. 16, 2023

(87) PCT Pub. No.: WO2022/128637
PCT Pub. Date: Jun. 23, 2022

(65) Prior Publication Data
US 2024/0032810 A1 Feb. 1, 2024

(30) Foreign Application Priority Data
Dec. 17, 2020 (EP) ..................................... 20214843

(51) Int. Cl.
*A61B 5/026* (2006.01)
*A61B 5/00* (2006.01)
(Continued)

(52) U.S. Cl.
CPC ........ *A61B 5/0261* (2013.01); *A61B 5/02427* (2013.01); *A61B 5/1075* (2013.01); *A61B 5/489* (2013.01); *G16H 30/40* (2018.01)

(58) Field of Classification Search
CPC . A61B 5/0261; A61B 5/02427; A61B 5/1075; A61B 5/489; G16H 30/40
See application file for complete search history.

(56) References Cited

U.S. PATENT DOCUMENTS

2017/0325686 A9 11/2017 Shan
2017/0367580 A1* 12/2017 DiMaio .................. A61B 5/445
(Continued)

FOREIGN PATENT DOCUMENTS

WO 2014140148 A1 9/2014
WO WO-2018148701 A1 * 8/2018 ........... A61B 5/0261

OTHER PUBLICATIONS

Blazek et al. 2018 in Multi-Modality Imaging, Chap. 2 p. 31-66 (Year: 2018).*
(Continued)

*Primary Examiner* — Keith M Raymond
*Assistant Examiner* — Patrick M Mehl

(57) ABSTRACT

The present invention relates to a device (100), systems (500, 500', 500") and a method for providing imaging of one or more aspects of blood perfusion induced by cardiac induced blood motion in a skin region (12) of a subject. Current perfusion imaging systems use either photoplethys-mography (PPG) or speckle contrast (SC), but a problem of both techniques is that considerable ambiguity exists because the source of the signal (volume pulsatility in PPG or blood flow in SC) is unknown. The present invention is based on the idea of combining two different types of measurement, namely widefield imaging and radial imaging, (Continued)

in order to estimate the source depth (20) of the signal to provide more accurate PPG imaging and SC imaging.

15 Claims, 17 Drawing Sheets

(51) Int. Cl.

| | | |
|---|---|---|
| *A61B 5/024* | (2006.01) | |
| *A61B 5/107* | (2006.01) | |
| *G16H 30/40* | (2018.01) | |

(56) References Cited

U.S. PATENT DOCUMENTS

| | | | |
|---|---|---|---|
| 2018/0310828 A1 | 11/2018 | DiMaio et al. | |
| 2019/0167124 A1* | 6/2019 | Verkruijsse | A61B 5/6826 |
| 2019/0175030 A1 | 6/2019 | Verkruijsse et al. | |
| 2023/0003595 A1 | 1/2023 | Zeng et al. | |
| 2023/0015851 A1 | 1/2023 | Verkruijsse et al. | |

OTHER PUBLICATIONS

Maeda et al. 2009 Optics & Laser Technology 41:755â763 (Year: 2009).*

Belaventseva et al. 2019 Proc. of SPIE 11024: 110240F 10 pages (Year: 2019).*

International Search Report and Written Opinion for PCT/EP2021/084611; Mailing date: Feb. 7, 2022, 9 pages.

Dunn, C. et al., "Comparison of speckleplethysmographic (SPG) and photoplethysmographic (PPG) imaging by Monte Carlo simulations and in vivo measurements", Biomedical Optics Express, 2018, vol. 9, Issue 9, pp. 4306-4316.

Harding, K., "Methods for addressing multiple reflections in a structured light profiler", Proceedings of SPIE 10991, Dimensional Optical Metrology and Inspection for Practical Applications VIII, 2019, 10 pages.

Verkruysse, W. et al., "Remote plethysmographic imaging using ambient light", Optics Express, 2008, vol. 16, Issue 26, pp. 21434-21445.

Verkruysse, W. et al., "Calibration of Contactless Pulse Oximetry", Anesthesia and Analgesia, 2017, vol. 124, No. 1, pp. 136-145.

Briers, J., "Laser Doppler and time-varying speckle: a reconciliation", Journal of the Optical Society of America A, 1996, vol. 13, No. 2, pp. 345-350.

Briers, D. et al., "Laser speckle contrast imaging: theoretical and practical limitations", Journal of Biomedical Optics, 2013, vol. 18, No. 6, 9 pages.

Sun, Y. et al., "Photoplethysmography Revisited: From Contact to Noncontact, From Point to Imaging", IEEE Transactions on Biomedical Engineering, 2016, vol. 63, No. 3, pp. 463-477.

* cited by examiner

PPG signal                    PPG image map          modulation depth
                                                     of PPG signal (AC/DC)

Reflected intensity $AC$ $DC$ time

40

$I(t)$                    $I(t)$                    Relative intensity of probing
                                                    light (contribution to signal)

13

16

12

14

Skin depth

A                         B

RAW speckle image
Low contrast   High contrast

Contrast image

Perfusion image

42

44

46 obtain data stream — S10 determine ODIs — S20 create ODI
image map — S30 create amplitude
image map — S40 correct amplitude
image map — S50

Correction for source depth wfPPG (x,y)

| | wfPPG | ODI | $C_{SD}$(ODI) | $PPG_{sdc}$ |
|---|---|---|---|---|
| Fh: | $5\times10^{-3}$ | 2 | 0.28 | $1.4\times10^{-3}$ |
| Chk: | $3\times10^{-3}$ | 5 | 0.87 | $2.6\times10^{-3}$ |

$PPG_{sdc}$: source depth corrected PPG amplitude $$PPG_{sdc}(x,y) = wfPPG(x,y) \times C_{SD}(ODI)$$

Option 1

ODI(x) discretized into ODIxi
j=13

DEVICE, METHOD AND SYSTEMS FOR PROVIDING IMAGING OF ONE OR MORE ASPECTS OF BLOOD PERFUSION

This application is the U.S. National Phase application under 35 U.S.C. § 371 of International Application No. PCT/EP2021/084611, filed on Dec. 7, 2021, which claims the benefit of European Application 20214843.3, filed Dec. 17, 2020. These applications are hereby incorporated by reference herein.

FIELD OF THE INVENTION

The present invention relates to a device, method and systems for providing imaging of one or more aspects of blood perfusion induced by cardiac induced blood motion in a skin region of a subject.

BACKGROUND OF THE INVENTION

Blood perfusion imaging gives access to information on the microcirculation (capillary, venular, arteriolar) of tissue and is of critical importance in diagnosis and therapeutical management of vascular diseases such as peripheral artery disease (PAD) and critical limb ischemia (CLI). Especially vascular surgeons and interventional radiologists are interested in both pre- and post-surgical monitoring of blood flow to improve medical care.

Current perfusion imaging systems are typically based on photoplethysmography imaging (PPGI) or speckle contrast imaging (SCI). Both imaging techniques comprise several similarities, but also some differences.

PPG generally refers to the measurement of volume changes of an organ or a body part and in particular to the detection of volume changes due to a cardiac vascular pulse traveling through the body of a subject with every heart beat. To be more concrete, PPG is an optical measurement technique that evaluates a time variant change of light reflectance or transmission of an area or volume of interest (such as a skin region) and is based on the principle that blood absorbs light more than surrounding tissue. Hence, variations in blood volume with every heart beat affect transmission or reflectance correspondingly. Further details about PPG imaging (PPGI) can, for example, be found in Verkruysse et al.: "Remote plethysmographic imaging using ambient light", Opt. Express 16 (26), 2008.

SCI is also an optical measurement technique that measures blood flow, and/or changes in blood flow, using laser speckle imaging. When laser light illuminates a diffuse area or a volume of interest, it produces a random interference effect known as a speckle pattern. If there is movement in the object, the speckles fluctuate in intensity and there is a connection between the fluctuations of the speckle pattern and the movement of scattering centers in living organisms, for example the movement of red blood cells. Averaging a region of interest from a speckle contrast image over time allows, similar to PPG, monitoring of heart rate and respiratory rate. Further details about the differences and similarities between PPG and SC can, for example, be found in Dunn et al.: "Comparison of speckleplethysmographic (SPG) and photoplethysmographic (PPG) imaging by Monte Carlo simulations and in vivo measurement", Biomedical Optics Express 9 (9), 2018.

WO 2018/148701 A1 discloses a sensor, such as a photoplethysmography sensor, for non-invasively monitoring a characteristic of an organism, such as a vital body sign. The sensor has multiple light sources disposed on a substrate and an array of optical probing channels for conveying light from the light sources to a probed region. Each detector pixel of an array of detector pixels receives light from a respective optical detection channel after interaction with a subregion of the probed region and spatial filtering, and generates a corresponding pixel signal. A processor derives a value of the vital body sign based at least upon the plurality of pixel signals.

US 2019/175030 A1 relates to a device, system and method for monitoring of peripheral arterial perfusion of a subject that address the problem that a low PPG signal can either result from a vascular stiffness or from a low cardiac output and that there is thus ambiguity in PPG measurements.

The images produced by PPGI and SCI typically suggest false colors that are proportional to perfusion which is induced by blood motion in the skin region to be investigated. However, a problem that arises for these images is that considerable ambiguity exists because the source of the signal, i.e., the source of the volume pulsatility in PPG or the blood flow in SC, is unknown. Due to Beer's law of attenuation, the signal dependency on source depth is exponential and the interpretation of false color images is thus very challenging. This means that a user has difficulties in interpreting perfusion images correctly because the false color in PPG and SC images represents the depth-integrated (non-linearly weighted) perfusion signal. Accordingly, a clinician cannot easily resolve this ambiguity which limits the commercial success of PPG and SCI imaging systems so far.

For these reasons, there is a need to provide a possibility of how this ambiguity can be resolved both for PPG and SCI to improve blood perfusion imaging.

SUMMARY OF THE INVENTION

It is an object of the present invention to provide means for improving SCI and PPGI, especially in order to ease the interpretation and accuracy of image maps, such as false color maps, for users. This would further lead to more commercial success of SCI and PPGI systems by becoming a common tool for medical staff, such as for vascular surgeons and interventional radiologists.

In a first aspect of the present invention, a device for providing imaging of one or more aspects of blood perfusion induced by cardiac induced blood motion in a skin region of a subject is presented. Said device comprises a processing unit, and this processing unit is configured to:

obtain data streams derived from detected electromagnetic radiation transmitted through or reflected from the skin region, said data streams comprising a data signal per skin pixel for a plurality of skin pixels of the skin region, wherein a first data stream is derived from a patterned illumination of the skin region and a second data signal is derived from a patterned illumination and/or homogenous illumination of the skin region;

determine, per skin pixel or group of skin pixels, from the data signals of the first data stream and the second data stream, optical depth indices, ODIs, by dividing, per skin pixel or group of skin pixels, data signals of the first data stream by data signals of the second data stream, wherein the ODIs are indicative of the depth of the blood flow within the skin region at the skin pixels or groups of skin pixels;

create an ODI image map of the skin region including the plurality of skin pixels from the determined ODIs;

create an amplitude image map of the skin region including the plurality of skin pixels from amplitudes of the data signals of the second data stream; and correct the amplitude image map by correcting, per skin pixel or group of skin pixels, the amplitudes of the data signals of the second data stream by the determined ODIs.

In another aspect of the present invention, there is provided a system for providing imaging of one or more aspects of blood perfusion induced by cardiac induced blood motion in a skin region of a subject. Said system comprises:

an illumination unit configured to emit a narrow radiation beam of electromagnetic radiation;

an optical diffuser configured to diffuse the electromagnetic radiation emitted by the illumination unit to illuminate the skin region of the subject homogenously and/or by a patterned illumination;

an imaging unit configured to detect the electromagnetic radiation transmitted through or reflected from the skin region of the subject and to derive data streams from the detected electromagnetic radiation; and a device as defined above.

Alternatively and in another aspect of the present invention, there is provided a system which comprises:

a first illumination unit configured to emit a pattern of electromagnetic radiation to illuminate the skin region of the subject by a patterned illumination;

a second illumination unit configured to emit a homogenous illumination profile to illuminate the skin region of the subject homogenously;

an imaging unit configured to detect the electromagnetic radiation transmitted through or reflected from the skin region of the subject and to derive data streams from the detected electromagnetic radiation; and a device as disclosed herein.

In yet further aspects of the present invention, there are provided a corresponding method and computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, systems, computer program and medium have similar and/or identical preferred embodiments as the claimed device, in particular as defined in the dependent claims and as disclosed herein.

The present invention is based on the idea that the considerable ambiguity that exists both for PPGI and SCI, because the source of the signal (volume pulsatility in PPG and blood flow in SC) is unknown, is resolved in that the depth of the source of the signal is determined. By this, imaging of one or more aspects of blood perfusion induced by cardiac induced blood motion in a skin region of a subject is enabled with higher quality. These aspects may, for example, be the volume pulsatility or the blood flow in the skin region to be investigated.

The images may, e.g., be displayed on a display unit that may be connected to the processing unit of the device. However, the processing unit on its own provides all the processing before in order to provide the imaging of one or more aspects of blood perfusion.

As mentioned above, one problem that arises in state of the art PPGI and SCI is that the false color represents the depth integrated (non-linearly weighted) perfusion signal and the current invention is thus based on the insight that the use of an optical depth index (ODI), which is an expression of the dominant optical depth of the source of the PPG or SC signal, allows improving PPGI and SCI notably.

The inventors realized that in order to determine this ODI, two different types of measurements are needed. These two different types are also called 'widefield imaging' and 'radial imaging' in the following as the first type of measurement, widefield imaging, is based on the principle that a skin region of a subject is illuminated homogenously (widefield exposure) and the PPG or SC signal is measured across that same skin region. This type of measurement is commonly used in camera mode since about a decade (see, e.g., Verkruysse et al.: "Remote plethysmographic imaging using ambient light", Opt. Express 16(26), 2008 or Y. Sun and N. Thakor: Photoplethysmography revisited: from contact to noncontact, from point to imaging, IEEE Trans Biomed Eng. 63(3), 2016).

It should be noted that the spatial integral of light reflected back from a patterned or structured illumination of the skin region can also be used for widefield imaging and the skin region does not necessarily be illuminated homogeneously for widefield imaging. Further, even just using a spot illumination (i.e., one laser spot on the skin region of the subject) and determining the spatial integral of all light reflected back from the skin region may also suitable for widefield imaging. Accordingly, the expression 'patterned illumination' may be an illumination with a single spot (e.g., laser spot) according to the present invention. However, often it might be better to use a homogenous illumination for the widefield imaging as this ensures a homogenous light distribution on the skin region to be investigated.

The other type of measurement, radial imaging, is based on the principle that a skin region is not illuminated homogenously, but rather by a patterned illumination, which again includes the possibility of illuminating the skin region with a single spot (e.g., laser spot). The pattern may, for example, be caused by several laser spots on the skin region of the subject, or may even be any illumination pattern with substantial spatial intensity fluctuations. In comparison to using a homogenous illumination, using a patterned illumination provides the advantage of gaining more signal strength in a few pixels as more light intensity is collected in a smaller area, which may be suitable to obtain more accurate SC and PPG signals due to a smaller signal-to-noise ratio.

A typical problem of widefield imaging is that in some tissues the widefield signal is too small to be measured (e.g., under arm or leg). This is likely due to arterioles being too deep. The low amount of light that reaches these depths (even in the red and infrared spectral range where the penetration depths are known to be larger than in other spectral ranges) is overwhelmed by light of much higher intensities that is remitted from shallower skin depths. In such cases, widefield imaging fails because the signal is too small and is overwhelmed by noise, e.g., of the detector and/or the illumination noise. This problem in imaging is also resolved by the present invention by using both widefield and radial imaging as radial imaging provides a large amount of light intensity on only a few skin pixels. This results in larger penetration depths of the electromagnetic radiation in the tissue and more signal strength.

The inventors realized that combining the data signals obtained from both measurements (widefield and radial imaging) allows resolving the depths from which the PPG and SC signals result from. This is a major advantage in comparison to prior art systems as these conventional imaging systems suggest, for example, that a relatively deep signal source (e.g., 0.5 mm below the epidermis) may give the same signal strength as a shallower vascular bed with much smaller perfusion located much closer to the epidermis (e.g., 0.1 mm below the epidermis).

In said context, it should also be noted that already the created ODI map according to the present invention gives a lot of insight into the blood motion in the investigated skin region because it allows investigating the different depths of pulsatile and non-pulsatile blood motion across the skin region.

According to the present invention, these new insights into the depth of the source are used to correct a conventional amplitude image map that represents the spatial distribution of the amplitude of the widefield PPG or widefield SC signal across the skin region. By this, the corrected amplitude image map provides much more accurate measurement results than the conventional image maps known in the art. Accordingly, a user, such as a clinician, can distinguish whether at a certain skin pixel the tissue is better perfused than at another skin pixel even though it might seem first that both these locations have the same perfusion strength (but which is not the case in reality).

In PPGI, the proposed technique provides source depth corrected image maps for the signal source (vessels with pulsatile volume). In SCI, the proposed technique provides source depth corrected image maps for two components of the signal: pulsatile blood flow and constant blood flow. This is explained in more detail later.

According to an embodiment, the processing unit is configured to correct the amplitude image map by estimating depths of the blood flow within the skin region at the skin pixels or groups of skin pixels from the determined ODIs. As mentioned above, the ODIs are an expression of the dominant or characteristic optical depths of the source of the PPG or SC signals at the respective skin pixels or groups of skin pixels. These ODIs thus are not a direct expression of the physical depth of the source of the signal. However, the inventors realized that these ODIs can be used to estimate the optical depths from which these signals (PPG signals or SC signals) come from. In this case, the processing unit is configured to correct the amplitude image map by correcting, per skin pixel or group of skin pixels, the amplitudes of the data signals of the second data stream by the estimated source depths of the blood flow.

Typically, the amplitudes of the data signals of the second data stream are proportional to $\exp(-2\mu_a SD)$, where pa is a predetermined tissue attenuation coefficient and SD is the estimated source depth of the blood motion within the skin region at a skin pixel or a group of skin pixels. This represents that the signal strength follows Beer's law. Beer's law relates the attenuation of light to the properties of the material through which the light is traveling and reflects that the signals that result from relatively deep positions below the epidermis are attenuated much more than the signals that result from positions much closer to the epidermis. Further, it reflects why considerable ambiguity exists because the source of the PPG or SC signal is unknown: the signal dependency on source depth SD is exponential and this non-linear dependency makes it difficult to interpret perfusion maps with an absence of depth information. This problem that constantly arises for conventional PPGI and SCI is hereby solved.

Due to Beer's law which defines that a large source depth SD leads to a large attenuation of a measured signal, the amplitudes of the data signals of the second data stream may be corrected by increasing the amplitudes in case where a large source depth is estimated from the ODIs, because the low signal amplitude is presumably not due to a low pulsatility but rather due to a large attenuation effect in this case. On the other hand, the amplitudes of the data signals of the second data stream may be corrected by decreasing the amplitudes in case where a small source depth is estimated from the ODIs. Another alternative possibility may be to correct the amplitudes that result from large source depths stronger than the amplitudes that result from small source depths in order to compensate for the attenuation effect. This correction can be either an increase or a decrease in amplitude.

Further, it shall be noted that the ODIs depend on the wavelength used for the measurement. However, the resulting ODI maps are, ideally at least, not wavelength dependent anymore, hereby eliminating yet another ambiguity of conventional perfusion maps. This is because the ODIs are implicitly wavelength dependent. The PPGI and SCI maps corrected for ODI are, ideally at least, not wavelength dependent anymore.

In case the widefield imaging measurements are performed by illuminating the skin region to be investigated by a patterned illumination, i.e., a pattern of dots, circles, lines, etc., the second detection signal is preferably derived by the processing unit by a spatial integral of the electromagnetic radiation transmitted through or reflected from the skin region. Accordingly, the data signals of the second data stream are obtained in that manner from raw image data streams transmitted, e.g., from a camera to the processing unit.

As mentioned above, the present invention is relevant for PPGI as well as for SCI. However, both optical measurement techniques are different and the processing of the data signals is different for the two measurement techniques. This is explained in the following, wherein it is first explained how the data signals are processed in case of PPG measurements followed by an explanation how the data signals are processed in case of SC measurements.

As known in the art, a PPG signal comprises two components, one alternating current (AC) and one direct current (DC) component. The AC component is dependent on the pulsatile blood flow and is therefore varying with the same frequency as the pulse. Since the AC component is directly connected to the pulsatile blood, it can be used to estimate the blood perfusion. The DC component is quasi-constant, and relates to what the tissue consists of in addition to the pulsatile blood. Accordingly, in case of PPG measurements, the data signals of the first and second data stream comprise time-varying AC components and constant DC components. In case of PPG measurements, the processing unit is preferably configured to create the amplitude image map by determining, per skin pixel or group of skin pixels, ratios of the time-varying AC components and the constant DC components of the data signals of the second data stream.

Further, in case the data signals are derived from PPG measurements, the processing unit may be configured to determine, per skin pixel or group of skin pixels, the ODIs from the data signals of the first and second data stream by dividing, per skin pixel or group of skin pixels, ratios of the time-varying AC components and the constant DC components of the data signals of the first data stream by ratios of the time-varying AC components and the constant DC components of the data signals of the second data stream. Accordingly, the ODIs are calculated by taking the ratios of the AC components and the DC components of the radial PPG signals and by dividing it by the ratios of the AC components and the DC components of the widefield PPG signals.

According to an embodiment, the processing unit may further be configured to determine, per skin pixel or group of skin pixels, the ODIs by selecting values of the ratios of the time-varying AC components and the constant DC components of the data signals of the first data stream at predetermined radial distances between the skin pixels or groups of skin pixels and illumination spots of the patterned illumination. In case of a patterned illumination with multiple illumination spots on the skin region, these radial distances may be the distances between the skin pixels and their closest illumination spot, i.e., the radial distance refers to the shortest distance between one illumination spot and a respective skin pixel. Preferably, these radial distances are substantially larger than 0, such as some millimeters for short wavelengths (such as for green light) and up to some centimeters for larger wavelengths (such as for red light). In case the data signals are derived from SC measurements, the processing of the data signals is different. This is explained in the following.

SCI is based on the principle that the backscattered light from a tissue that is illuminated with coherent light, such as coherent laser light, forms a random interference pattern at the detector or imaging unit, the so-called raw speckle pattern. Movement of particles inside the tissue causes fluctuations in this speckle and the perfusion signals which are derived from the raw speckle pattern comprise pulsatile and non-pulsatile, constant components (cf. also D. Briers et al.: "Laser speckle contrast imaging: theoretical and practical limitations", Journal of Biomedical Optics, 2013 for more details). The pulsatile components represent the cardiac induced pulsatile blood motion in vessels of the investigated skin region and the constant components represent the averaged non-pulsatile blood motion in vessels of the investigated skin region.

Even though the AC components and DC components of PPG signals are also often called 'pulsatile components' and 'constant components' in the art, the expressions 'pulsatile component' and 'constant component' are only used for components of the perfusion signals in SCI in the following. For PPG, the components are called 'AC component' and 'DC component'. This allows it to differentiate how the PPG data signals and the SC data signals are processed differently according to the present invention.

In an embodiment where the optical measurements are based on the SC technique, the data signals of the first and second data stream may comprise pulsatile components and/or constant components. Further, in this embodiment, the processing unit is configured to create the amplitude image map from the pulsatile or the constant components of the data signals second data stream. This means that a pulsatile widefield SCI map or a constant widefield SCI map is created from the data signals of the second data stream. Hence, in difference to PPG where the amplitude image map is created by taking the ratios of the time-varying AC components and the constant DC components, in case of SCI, the amplitude image map is created by taking either the pulsatile components or the constant components (and not by taking ratios as for PPG). Preferably, an amplitude image map is created for both the pulsatile components and the constant components, for example, by creating first the pulsatile amplitude image map and then the constant amplitude image map. In this case, insight is given into the pulsatile blood flow in vessels as well as into the averaged non-pulsatile blood flow in vessels.

Hence, although the primary data signals for PPG and SCI appear very similar, there is an important difference. In PPG, the normalization of the AC component with the DC component makes sense since the data signals comprise information related to the light intensity and the normalization cancels out said light intensity as both the AC component and the DC component are proportional to it. In SCI, the primary data signals are perfusion signals as known in the art of SCI (cf. also D. Briers et al.: "Laser speckle contrast imaging: theoretical and practical limitations", Journal of Biomedical Optics, 2013 or Dunn et al.: "Comparison of speckleplethysmographic (SPG) and photoplethysmographic (PPG) imaging by Monte Carlo simulations and in vivo measurement", Biomedical Optics Express 9 (9), 2018). Accordingly, a normalization as in PPG does not make sense. Rather the pulsatile components or the constant components are processed as separate independent components according to the present invention.

In case of SCI, the processing unit may further be configured to determine, per skin pixel or group of skin pixels, the ODIs from the data signals of the first and second data stream. Here, a distinction between the pulsatile components and the constant components is needed. For the pulsatile components, the ODIs may be calculated by dividing, per skin pixel or group of skin pixels, the pulsatile components of the data signals of the first data stream by the pulsatile components of the data signals of the second data stream. For the constant components, the ODIs may be calculated by dividing, per skin pixel or group of skin pixels, the constant components of the data signals of the first data stream by the constant components of the data signals of the second data stream.

According to an embodiment, the processing unit may further be configured to determine, per skin pixel or group of skin pixels, the ODIs by selecting values of the pulsatile or constant components of the data signals of the first data stream at predetermined radial distances between the skin pixels of groups of skin pixels and illumination spots of the patterned illumination. In case of a patterned illumination with multiple illumination spots on the skin region, these radial distances may be the distances between the skin pixels and their closest illumination spot.

The systems for providing imaging of one or more aspects of blood perfusion induced by cardiac induced blood motion in a skin region of a subject according to the present invention may either be a system with one illumination unit configured to emit a narrow radiation beam of electromagnetic radiation, such as a laser, and with an optical diffuser configured to diffuse said electromagnetic radiation or a system with two illumination units (a first illumination unit and a second illumination unit) which are configured to generate the different illumination profiles on the skin of the subject that are needed for widefield imaging and radial imaging. In case the system comprises only one illumination unit, the diffuser may selectively be arranged within or outside of the path of the emitted light of the illumination unit. In this case, the diffused widefield illumination may be obtained by arranging the optical diffuser inside the path of light and the radial illumination (such as a single laser spot) may be obtained by arranging the optical diffuser outside the path of light. Further, the optical diffuser may be configured such that a structured or patterned illumination with a plurality of circles, lines, dots, etc. is obtained on the skin region to be investigated.

In an embodiment, the imaging unit may comprise an optical sensing array, in particular a two-dimensional image sensor, including a filter (such as a bandpass filter) providing at least two different wavelength channels, and the illumination unit may be configured to emit electromagnetic radiation for illuminating the skin region of the subject with light in said at least two different wavelength channels. A two-dimensional image sensor allows measuring images and a lateral distribution of the measured PPG or SC signals. Instead of using one imaging unit, it may also be an option to use two different imaging units, such as two different cameras, equipped with bandpass filters for the two different wavelengths $\lambda 1$ and $\lambda 2$ of the emitted electromagnetic radiation. Further, the wavelengths $\lambda 1$ and $\lambda 2$ are preferably chosen such that they are very close (such as below 50 nm difference for red light and below 10 nm difference for green light) to ensure that optical properties are very similar, small enough to not affect the penetration depths appreciably. The passbands of the bandpass filters have to be very small in this case. Choosing wavelengths for which optical properties (absorption and scattering) are very similar is possible by choosing the wavelengths to be in a region where blood absorption does not change appreciably (e.g., in the electromagnetic range around 660 nm). Alternatively, the measurements can be performed by choosing the wavelengths $\lambda 1$ and $\lambda 2$ to be in the red or infrared spectral range as these spectral ranges are known to be suitable for perfusion measurements due to the larger penetration depth of electromagnetic radiation in the skin of the subject at said spectral ranges. Hence, it is possible to reach deeper vessels for measurements in the red and near-infrared spectral range.

Last but not least, it shall be mentioned that the illumination unit and the imaging unit may either both be in direct physical contact to the skin region of the subject or not in direct physical contact to the skin region of the subject. Hence, the present invention may, e.g., be implemented by using a conventional finger tip sensor which is attached to the skin of the subject or by performing remote measurements, such as remote PPG (see Verkruysse et al.: "Remote plethysmographic imaging using ambient light", Opt. Express 16(26), 2008 for more details), where the illumination unit as well as the imaging unit are not in direct physical contact to the skin of the subject.

Further advantages result from the description and the attached drawings. It shall be understood that the features mentioned above and below may be used not only in the combinations indicated, but also in other combinations or as a whole, without leaving the framework of this invention.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figures 1, 2:
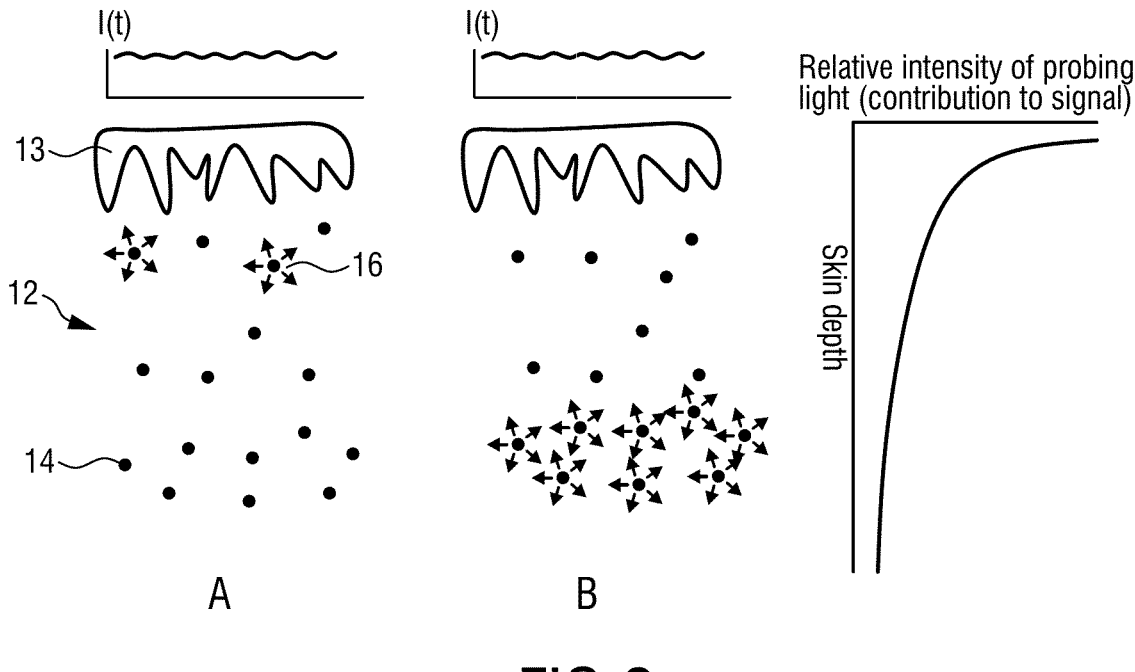
FIG. 1 shows a conventional PPG amplitude image map which is created by PPG measurements as known in the art on the head of a subject.
FIG. 2 shows a schematic diagram illustrating how ambiguity in the interpretation of the modulation depth is caused by a strong dependence of the measured signal with skin depth.

FIG. 1 shows a conventional PPG amplitude image map 40 which is created by PPG measurements as known in the art on the head of a subject. PPG can be used to detect blood volume changes in the microvascular bed of tissue and these changes in volume are detected by illuminating the skin with light from an illumination unit, such as an LED, and then measuring the amount of light either transmitted or reflected to an imaging unit, such as a camera. The diagram on the left of FIG. 1 shows exemplarily the reflected intensity of such a measured PPG signal and illustrates that a PPG signal comprises two components: a pulsatile waveform (AC) attributed to changes in the interrogated blood volume with each heart beat, and a constant baseline (DC) or offset combining only low frequency fluctuations mainly due to respiration and sympathetic nervous system activity.

A conventional PPG amplitude image map 40 as shown in FIG. 1 is created by determining for each skin pixel or group of skin pixels the ratio of the AC component and DC component. The amplitude AC/DC (modulation depth of PPG signal) is typically imaged as false color. As shown in FIG. 1, the modulation depth of the PPG signal on the forehead is typically large (with a maximum modulation depth of almost $5 \times 10^{-3}$ in this example).

A problem that arises for such conventional PPG imaging (PPGI) is that the amplitude of the PPG signal does not give unambiguous information regarding skin blood perfusion. Skin pixels A and B in FIG. 1 may give the same PPG amplitude, but it is unclear to the user, such as a clinician, why this is exactly the case.

FIG. 2 shows a schematic diagram illustrating how ambiguity interpretation of modulation is caused by a strong dependence of the measured signal with skin depth. Even though, the modulation depths (amplitude strengths) for skin pixels A and B are the same in FIG. 1, the source of the signal may be completely different as it is shown in FIG. 2.

The epidermis 13 of a skin region 12 and the underlying non-pulsatile vessels 14 and pulsatile vessels 16 are illustrated in FIG. 2. It can be seen that the signal I(t) at skin pixel A is caused by a few pulsatile vessels that are located close to the epidermis 13. On the other hand, the signal measured at skin pixel B is caused by much more pulsatile vessels at much larger depths. Hence, the relative overall skin perfusion is much higher at skin pixel B than at skin pixel A since more vessels are pulsatile (indicating arterial supply, which can serve the tissue with oxygen and take away the CO2, at skin pixel B is larger than at skin pixel A).

The equal PPG amplitude for skin pixels A and B in FIGS. 1 and 2 can be understood by realizing that the light reaching the deeper pulsatile vessels at skin pixel B is of much lower intensity than light reaching the pulsatile vessels at skin pixel A. This can be seen by the non-linear behavior of the relative intensity of probing light in dependence on the skin depth that is shown in the diagram of FIG. 2. This means nothing else than that a conventional PPG amplitude image map is ambiguous as depth information are missing.

Besides the depth dependency, another ambiguity present in perfusion maps is that the wavelength used is a factor while this is typically not mentioned explicitly in the art. Neither is this wavelength dependency known by users of perfusion imaging devices. When highly penetrating wavelengths are used, the perfusion maps will likely differ from those measured with a less penetrating wavelength (e.g. green).

Figure 3:
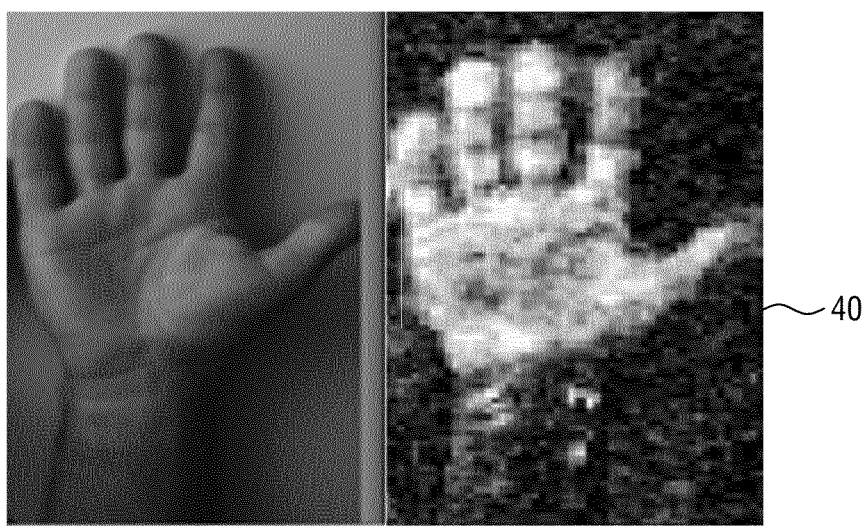
FIG. 3 shows a picture and a corresponding conventional PPG amplitude image map of a hand of a subject.

FIG. 3 shows a picture and a corresponding conventional PPG amplitude image map 40 of a hand of the subject. Increased PPG amplitudes at fingertips, lower amplitudes at the center inside the palm and much lower amplitudes at the arm are typically measured (bright pixels represent a large PPG amplitude (AC/DC) in FIG. 3). However, the measured differences in the amplitudes between nearby locations are more likely due to the different depths of local vasculature than variations in the local perfusion.

This problem of ambiguity is not limited to PPG as the same problem also occurs for speckle contrast imaging (SCI). Light used for the laser speckle contrast analysis is attenuated as it progresses to deeper skin depths. As a result, the flow in deeper blood vessels has a smaller impact on the total perfusion signal than the flow in shallower vessels. Accordingly, conventional SCI perfusion images suffer from the same ambiguity as the PPG images.

Figure 4:
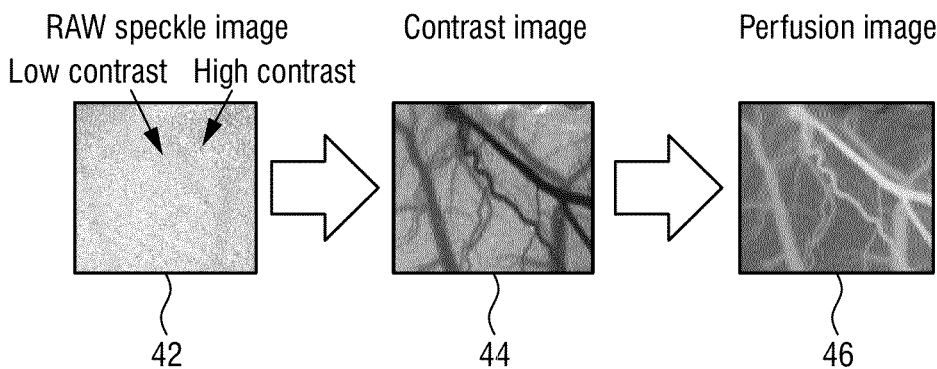
FIG. 4 shows a schematic diagram which illustrates how SC perfusion images are commonly generated.

FIG. 4 shows a schematic diagram which illustrates how SC perfusion images are commonly generated. SCI is an optical measurement technique that measures changes in the blood flow using laser speckle imaging. When laser light illuminates a diffuse area or a volume of interest, it produces a random appearing interference effect known as raw speckle pattern. This raw speckle pattern 42 can be seen in FIG. 4 and is in fact a deterministic interference pattern. If there is movement in the volume of interest, the speckle pattern changes since the underlying scattering particles and structures change their location. These fluctuations can provide information about the movement of blood. With a finite exposure time, a photographic recording will appear somewhat blurred if the speckle pattern changed during that period of time. So, the reduced contrast can be understood by realizing that the interference pattern changes due to different positions of the scatters. A decreased speckle contrast can also be understood in terms of a Doppler widening which is caused by moving particles, such as blood cells, which scatter off. Accordingly, such a raw speckle image 42 comprises sections or locations with a high contrast as well as locations with a low contrast where the fluctuations cause blurring of the speckles, leading to a reduction in the local speckle contrast. So, the reduced contrast can be understood by realizing that the light is less monochromatic after scattering as when a photon scatters from a moving particle, its carrier frequency is Doppler shifted.

Accordingly, the raw speckle image 42 comprises a temporal aspect: a static laser speckle pattern represents that there is no movement of blood cells and a dynamic pattern indicates that there is movement of blood cells.

In a subsequent step, a contrast image 44 is generated from the raw speckle image 42 and in the last step, a final perfusion image 46 is generated from the contrast image 44, wherein the perfusion is typically proportional to an inverse of the contrast and to the blood flow velocity and volume of flowing blood. By comparing the final perfusion image 46 and the raw speckle image 42, it becomes apparent that the locations with a low contrast have a high perfusion. Accordingly, the contrast image comprises a spatial aspect: a high contrast represents that there is no movement of blood cells and a low contrast represents that there is movement of blood cells.

However, also here, as for the PPG images discusses earlier, it is unclear whether the high perfusion at certain locations is either caused by a very strong perfusion in deep vessels or by a rather moderate perfusion in shallower vessels. Accordingly, also the interpretation of conventional perfusion images is ambiguous due to the absence of depth information.

Figure 5:
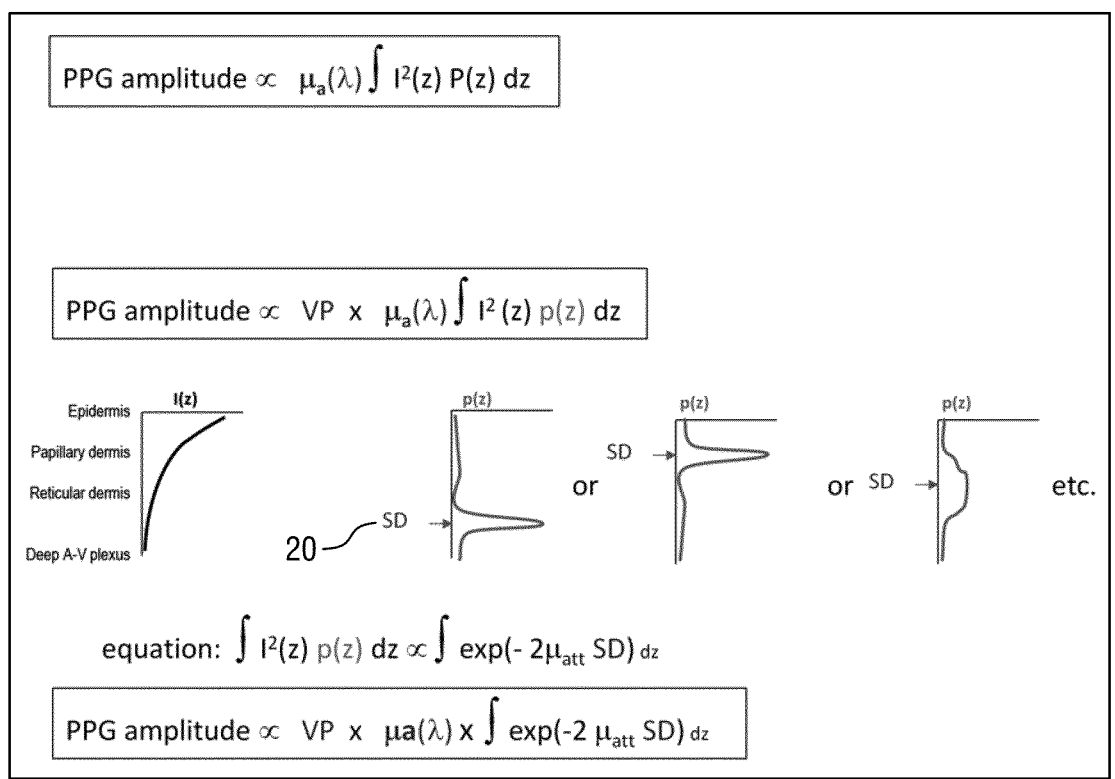
FIG. 5 shows a schematic diagram which illustrates that a measured PPG signal depends on volume pulsatility, tissue attenuation and source depth.

FIG. 5 shows a schematic diagram which illustrates that a measured PPG signal depends on volume pulsatility VP, tissue attenuation pa and source depth SD. Light in tissue can be modeled with Beer's law which relates the attenuation of light to the properties of the material through which the light is traveling. The attenuation coefficient $\mu_a$ can be reasonably determined from known optical and tissue properties. As shown in the upper part of FIG. 5, it is assumed that the PPG amplitude is proportional on said attenuation coefficient $\mu_a$, P(z) and the intensity I(z), wherein P(z) can be replaced by p(z) and VP, and z is the tissue travel distance of the light penetrating into the skin region. VP is the overall volumetric pulsatility which can greatly vary from person to person, or within a person as a result of ambient temperature, for example. The expression p(z) represents the pulse at the arteriolar level (local pulsatile profile in the arterioles) which may change upon different shunt status at the skin level and which depends on the depths of the arterioles. Similarly, also the tissue attenuation coefficient $\mu_a$ varies greatly since it is highly dependent on wavelength. However, by using a known wavelength of the emitted light, said attenuation coefficient $\mu_a$ can be reasonably determined from known tissue properties. In general, $\mu_a$ is not dependent on p(z) but on the total amount of chromophores and scattering properties of the tissue to be investigated.

By defining a dominant source depth SD from which the measured PPG signal results from, it is possible to replace p(z) and I(z) from the second equation in FIG. 5 to obtain the final expression where the PPG amplitude only depends on three factors: volume pulsatility VP, tissue attenuation pa and source depth SD. It is thus assumed that the PPG amplitude is linearly proportional to the overall volumetric pulsatility VP of vessels, linearly proportional to the attenuation coefficient $\mu_a$ and non-linearly proportional to the source depth SD of the pulsatile vessels (i.e., light has to travel down a distance SD to the pulsatile vessels and back to the skin surface).

Accordingly, extracting depth information allows determining a corrected PPG amplitude. It is possible to ratio-out VP and $\mu_a$ from the last equation in FIG. 5 to obtain an expression for the PPG amplitude that is highly (if not uniquely) dependent only on geometry, i.e., the source depth SD. This is the rationale behind the approach of the present invention to determine an ODI, which is explained later, for the source of a PPG signal. The same principle applies for the source of a SC signal and it shall be understood that the calculations shown in FIG. 5 are thus only exemplarily made for PPG.

Further, it shall be noted that it may be an option to model the light in tissue with Beer's law and different attenuation coefficients for the systole and diastole. In this way it is possible to find an expression for the PPG amplitude AC/DC that depends only on the tissue travel distance z and the difference between the systolic and the diastolic attenuation coefficient. Accordingly, also this model allows estimating a source depth of the PPG signals (i.e., of the volume pulsatility at that depth).

Figures 6A, 6B, 7A, 7B:
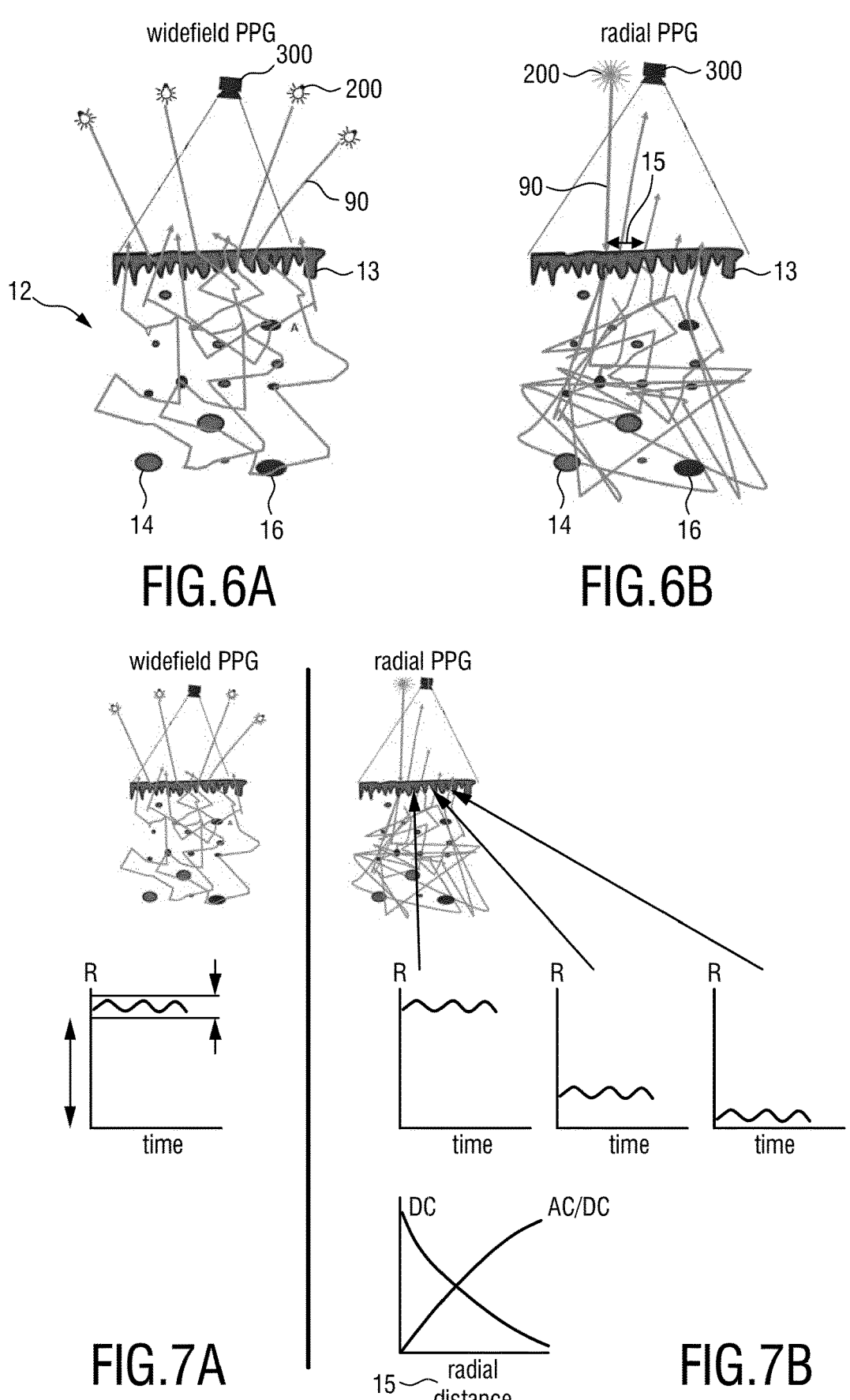
FIGS. 6A and 6B show schematic diagrams illustrating the path of electromagnetic radiation through a skin region of a subject for widefield PPG and radial PPG.
FIGS. 7A and 7B show schematic diagrams illustrating the detected reflected light for widefield PPG and radial PPG.

FIGS. 6A and 6B show schematic diagrams illustrating the path of electromagnetic radiation 90 through a region skin 12 of a subject for widefield PPG and radial PPG. The present invention combines two different measurement types: widefield imaging and radial imaging. FIGS. 6A and 6B show exemplarily how these two different measurement types can be performed in case of PPG measurements. Widefield PPG is the mode that is commonly used in camera mode for various years, where the illumination by electromagnetic radiation 90 from an illumination unit 200 is homogeneously distributed across the skin region 12 and the PPG signal is measured across that same skin region. This mode is shown in FIG. 6A. The electromagnetic radiation 90 travels through the skin region 12 with non-pulsatile vessels 14 and pulsatile vessels 16 before getting detected by an imaging unit 300, such as a camera. The detected electromagnetic radiation 90 and the derived PPG signal is an average of all the electromagnetic radiation 90 detected by the camera 300.

FIG. 6B shows a radial PPG mode. Radial PPG is in principle quite similar to conventional contact probe PPG measurements. The skin region 12 is illuminated by a spot (or a pattern such as a pattern of circles, stripes, dots, etc.) and the PPG signal is measured several millimeters away from that one or more illumination spots on the skin region 12. This radial distance 15 between one illumination spot on the skin region 12 and the spot from which the PPG signal is measured is exemplarily illustrated for one reflected beam in FIG. 6B. Hence, the radial PPG signal is in general a signal which depends on the radial distance 15. In other words, the electromagnetic radiation 90 reflected from the skin region 12 of the subject is reflected from said skin region by entering into the skin region through the epidermis at the illumination spot, getting reflected from constituents of the skin region and exiting the skin region through the epidermis 13 at a radial distance 15 from the illumination spot (typically some millimeters or centimeters away from the illumination spot). By this, the electromagnetic radiation 90 detected by the imaging unit 300 is scattered back from the skin region 12 and collects pulsatile information from the different non-pulsatile vessels 14 and pulsatile vessels 16 located in the skin region 12 below the epidermis 13.

It will be shown later that the present invention combines the results obtained from these two different measurement types (radial PPG imaging and widefield PPG imaging). The same applies for SC measurements where also the results obtained from radial and widefield imaging are combined.

FIGS. 7A and 7B show schematic diagrams illustrating the detected reflected light for widefield PPG and radial PPG. The schematic diagrams on the top of FIGS. 7A and 7B are the same that have already been discussed with reference to previous FIGS. 6A and 6B.

FIG. 7A shows (on the bottom) a diagram illustrating the detected reflected light of a widefield PPG setup. For this purpose, the axis of ordinate illustrates the reflected detected light and the axis of abscissae illustrates the measurement time. The curve illustrates the reflected detected light which comprises a DC component and an AC component. The AC component represents the pulsatile components of optical absorption originating from the pulsatile arterial blood and the DC component represents the non-pulsatile component containing contributions from non-pulsatile arterial blood, venous blood and other tissues.

FIG. 7B shows in the middle row three diagrams illustrating the detected reflected light of a radial PPG setup. For this purpose, the axes of ordinate illustrate again the reflected detected light and the axes of abscissae illustrate the measurement time. It becomes apparent from the three curves that the longer the light has travelled through skin of the subject (and the larger the radial distance 15, cf. FIG. 6B), the smaller the DC component of the reflected detected light is. This is schematically illustrated by the offset of the three different curves, respectively. The reason for this is that more light or electromagnetic radiation 90 is absorbed and/or scattered by the skin region 12 if the light travels through skin by a longer path. Accordingly, the DC component is reduced.

This dependency is also illustrated in the lowermost diagram of FIG. 7B. This diagram illustrates the AC or DC component of the reflected detected light on the axis of ordinate and radial distance 15 on the axis of abscissae. One curve illustrates the DC component of the reflected detected light and the other curve illustrates the ratio AC/DC of the reflected detected light. The already discussed trend becomes apparent. Further, it becomes clear that the larger the radial distance 15, the larger the ratio AC/DC is (the larger the relative pulsatile component is).

Figure 8:
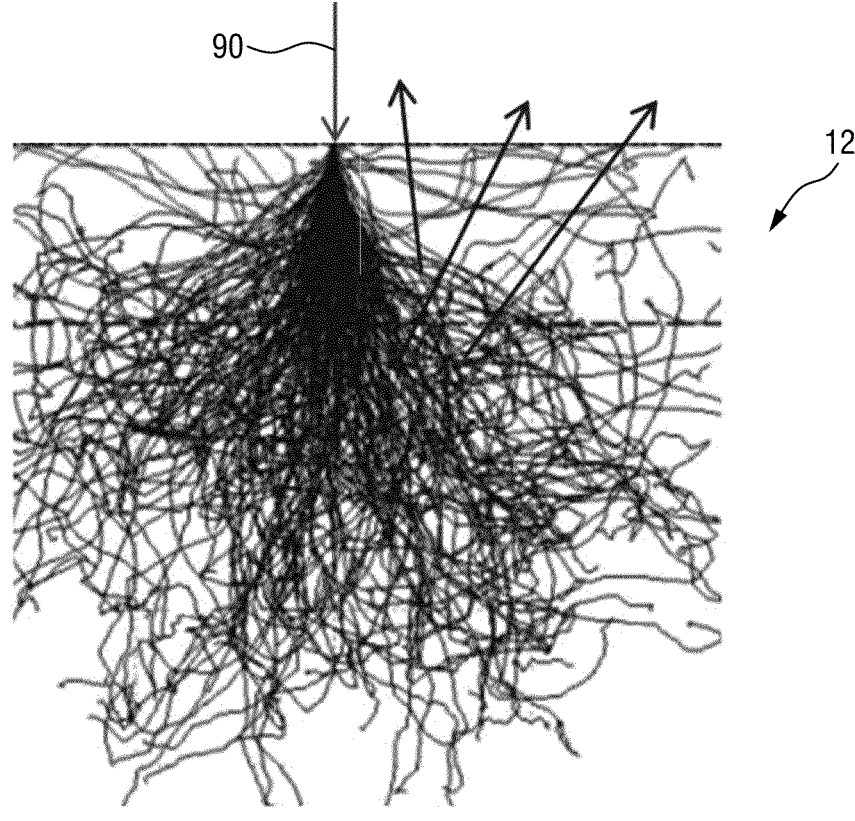
FIG. 8 shows a schematic diagram of Monte Carlo simulations of the path of light through the skin region of a subject for radial PPG measurements.

FIG. 8 shows a schematic diagram of Monte Carlo simulations of the path of light through the skin region 12 of a subject for radial PPG measurements. The light distribution inside the skin region 12 is visualized to illustrate the different penetration depths.

Figures 9A, 9B:
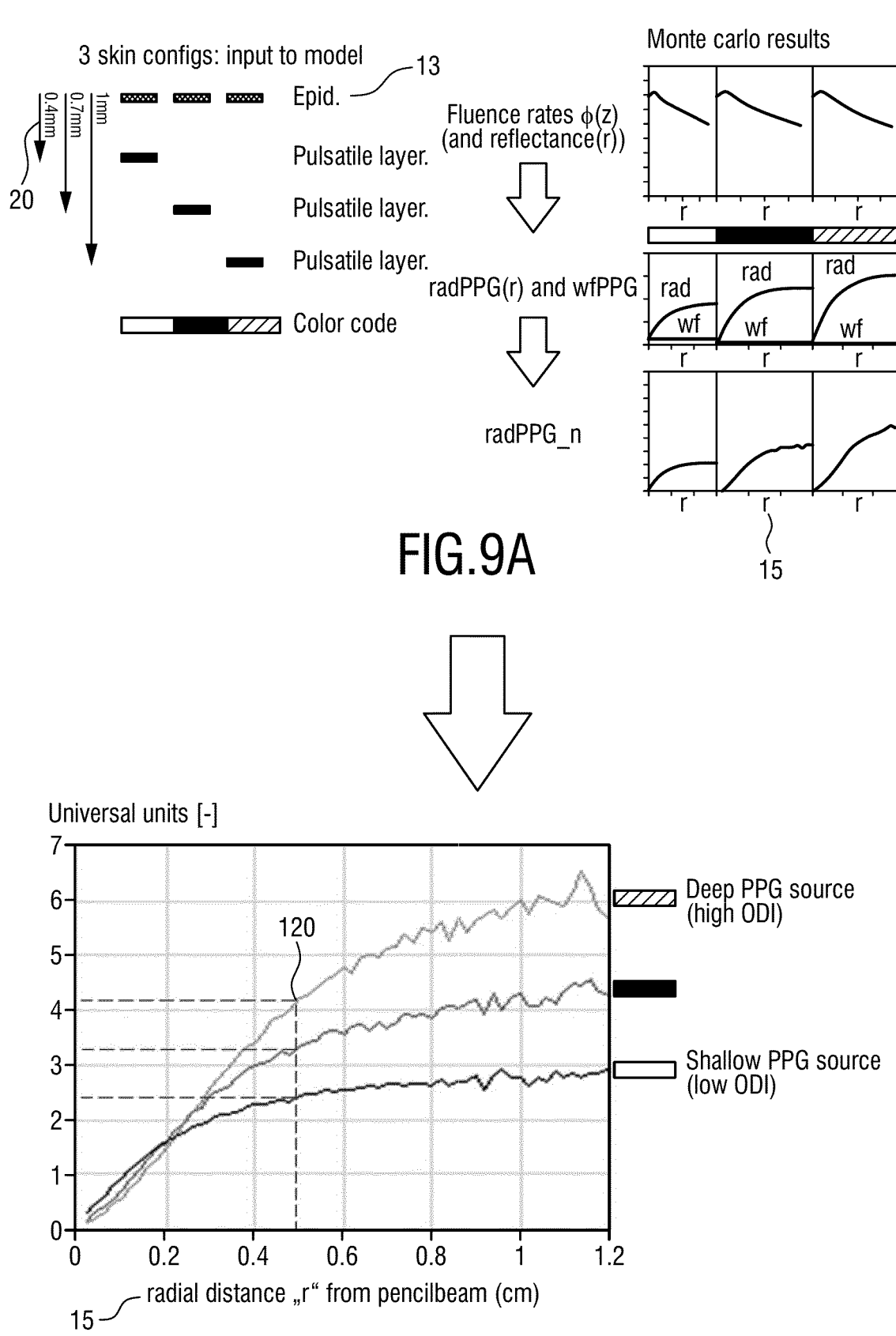
FIGS. 9A and 9B show Monte Carlo results of three different skin configurations with shallow, medium and deep pulsatile layers.

FIGS. 9A and 9B show Monte Carlo results of three different skin configurations with shallow, medium and deep pulsatile layers. The shallow, medium and deep pulsatile layers have different source depths 20 of 0.4 mm, 0.7 mm and 1 mm. It can be seen in the Monte Carlo results that the source depths 20 of the pulsatile layers have an impact on the amplitudes of both widefield PPG and radial PPG. The amplitudes of widefield PPG signals decrease with increasing source depth 20 while the amplitudes of the radial PPG signals increase. This can be seen in FIG. 9A where the amplitudes of the radial PPG signals (radPPG(r)) are largest for the deepest pulsatile layer (which is located at a skin depth 20 of 1 mm) and the amplitudes of the widefield PPG signals (wfPPG) are largest for the shallowest pulsatile layer (which is located at a skin depth 20 of 0.4 mm).

The lowest diagrams in FIG. 9A show the normalized radial PPG signals (RadPPG_n) which are determined by dividing the radPPG(r) signals by the wfPPG signals. The inventors realized that this expression RadPPG_n allows estimating a dominant source depth of the pulsatile layers. This is illustrated in FIG. 9B where the RadPPG_n curves are again shown on a larger scale. The larger the amplitude of the RadPPG_n curves, the higher an ODI which is indicative of the depth of the blood flow within the skin region.

To summarize, in case of PPG, the determination of the ODIs may be done by combining widefield PPG and radial PPG, more specifically, by normalizing the radPPG(r) signals by the widefield PPG signals: radPPG_n(r)=radPPG(r)/wfPPG and subsequently by taking the ODI as the value of radPPG_n(r) at a predetermined radial distance.

It shall be understood that these principles also apply for the SC measurements. Analogous to the ODI determination for the PPG modulation depth, the ODIs for SCI may be determined by selecting the value for radSCI(r)/wfSCI at a predefined distance R, such as at 0.5 mm as shown exemplarily for PPG in FIG. 9B. In the example of FIG. 9B for PPG measurements, the ODI for R=0.5 mm would be determined as ODI=2.2, 3.2 and 4.1 for the shallow, medium and deep pulsatile layers, respectively.

Figure 10:
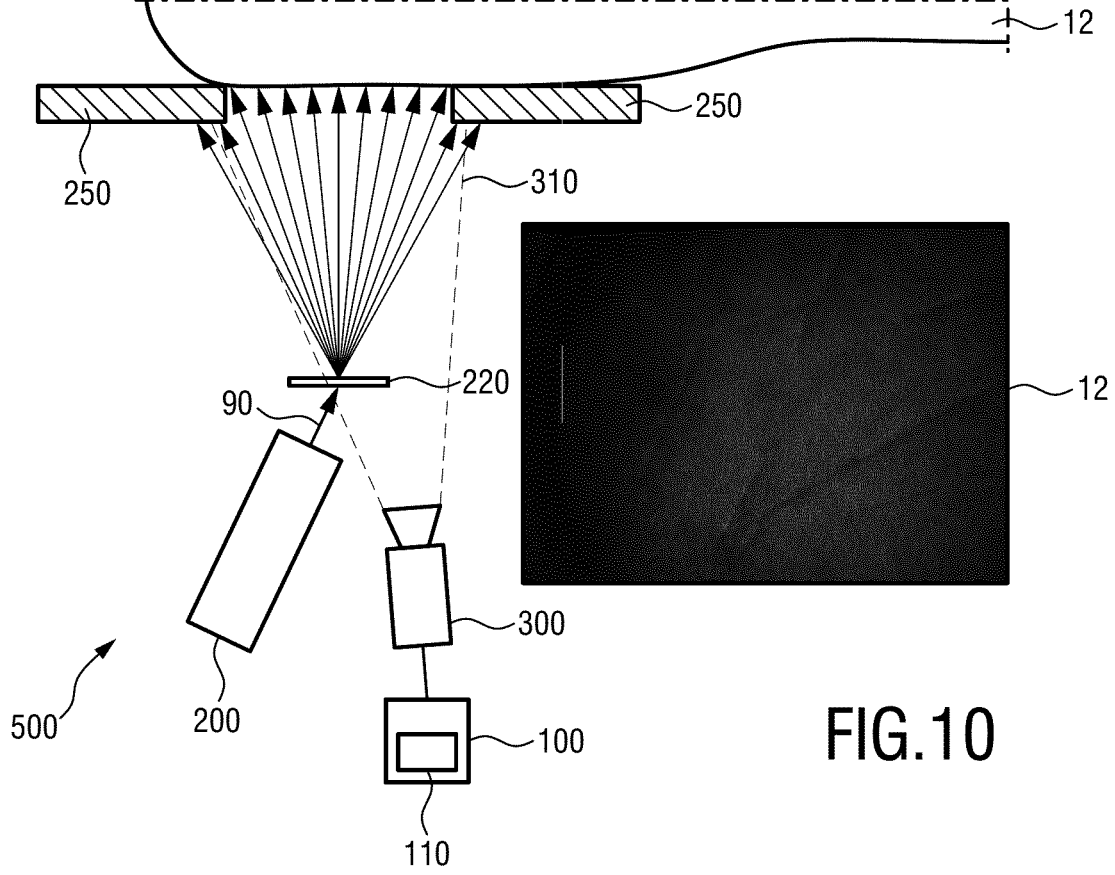
FIG. 10 shows a system for providing imaging of one or more aspects of blood perfusion induced by cardiac induced blood motion in a skin region of a subject according to the present invention.

FIG. 10 shows a system 500 for providing imaging of one or more aspects of blood perfusion induced by cardiac induced blood motion in a skin region 12 of a subject according to the present invention.

As shown in FIG. 10, the system 500 at least comprises an illumination unit 200, an imaging unit 300 and a device 100 with a processing unit 110 for providing imaging of one or more aspects of blood perfusion induced by cardiac induced blood motion in a skin region 12 of a subject. A more detailed explanation of said device 100 will be given below with reference to FIG. 12.

The illumination unit 200 is configured to emit electromagnetic radiation 90 to illuminate the skin region 12. Preferably, said illumination unit 200 is configured to emit a controllable narrow beam of electromagnetic radiation 90. The electromagnetic radiation 90 is further preferably located in the visible and infrared spectral range. Accordingly, the illumination unit 200 may also be configured to emit electromagnetic radiation 90 at at least two different wavelengths and/or to alternately emit, for example, visible and infrared light as electromagnetic radiation 90. One difference between SCI and PPGI is that for SC measurements, the emitted light must be coherent while for PPG measurements the emitted light does not necessarily be coherent. However, in case a coherent light source is used as the illumination unit 200, SCI and PPGI can both be extracted from the same video sequences that may be recorded by using the same (conventional) camera as the imaging unit 300.

According to the embodiment shown in FIG. 10, the system 500 may optionally further comprise a support 250 for limiting the skin region 12 of the subject to a limited skin area to be measured. This support 250 may be placed on the skin of the subject as shown in FIG. 10 and is preferably made of a material that is non-transparent for the incoming electromagnetic radiation 90 in the visible or infrared spectral range. Preferably, the skin region 12 used for measurement is thus limited to an area which comprises a skin part with a homogenous surface along the area to be measured. This increases the measurement accuracy.

Additionally, the system 500 shown in FIG. 10 further comprises a diffuser 220. Said diffuser 220 is configured to diffuse the controllable narrow beam of electromagnetic radiation 90 emitted by the illumination unit 200 to generate a homogenous illumination profile and/or a pattern of dots, circles, stripes etc. on the skin region 12 of the subject. The imaging unit 300 is preferably a camera configured to detect electromagnetic radiation 90 in the visible and infrared spectral range. The camera 300 is located such that the field of view covers the skin region 12 illuminated by the illumination unit 200.

It should be noted that widefield PPG or widefield SC cannot only be measured if the skin 12 of the subject is illuminated homogenously. It works as well if the skin region 12 is illuminated by a pattern, such as a spot pattern (dots, circles, stripes, etc.), or just by a single spot. In that case, the PPG or SC signal is derived by a spatial integral of preferably all the electromagnetic radiation 90 transmitted through or reflected from the skin region 12. The processing unit 100 may be configured to perform said spatial integration. Further, it should be noted that the generation of a homogenous illumination profile on the skin region 12 of the subject cannot only be obtained by using an illumination unit 200 configured to emit a controllable narrow beam (such as a laser) and a diffuser 220 to diffuse said narrow beam, but also by using one or even more illumination units that directly emit a homogenous illumination profile, such as a bulb. This becomes apparent from subsequent FIG. 11.

In case the system comprises only one illumination unit (as shown in FIG. 10), the diffuser 220 may selectively be arranged within or outside of the path of the emitted light of the illumination unit 200. In this case, a diffused widefield illumination may be obtained by arranging the optical diffuser inside the path of light and a radial illumination (such as a single laser spot) may obtained by arranging the optical diffuser inside the path of light.

Figure 11:
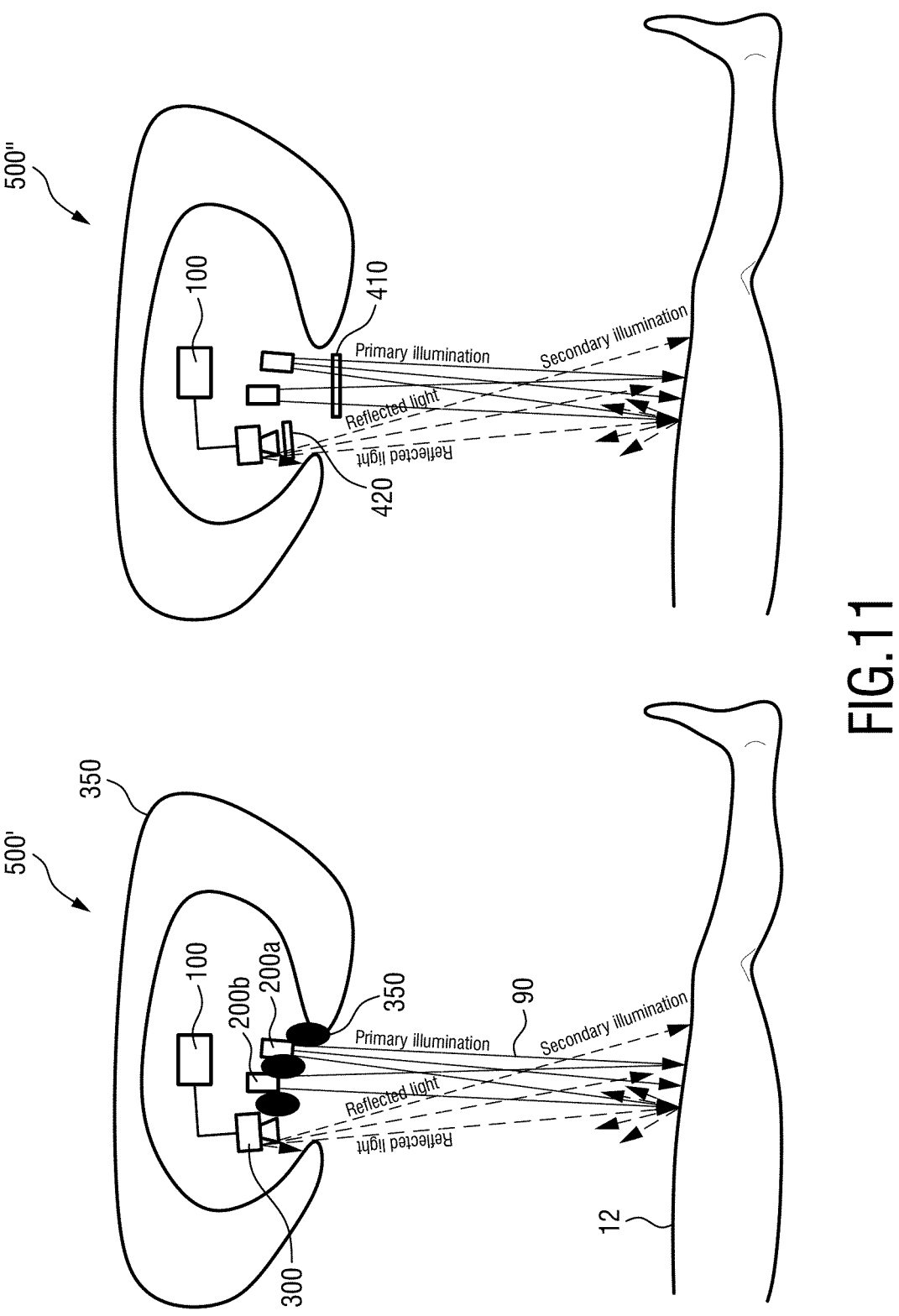
FIG. 11 shows further systems for providing imaging of one or more aspects of blood perfusion induced by cardiac induced blood motion in a skin region of a subject according to the present invention.

FIG. 11 shows further systems 500', 500" for providing imaging of one or more aspects of blood perfusion induced by cardiac induced blood motion in a skin region 12 of a subject according to the present invention.

As shown for both systems 500, 500", it is also a possibility to use two different illumination units 200*a*, 200*b*, wherein a first illumination unit 200*a* is configured to emit a pattern of electromagnetic radiation 90 to illuminate the skin region 12 of the subject by a patterned illumination and a second illumination unit 200*b* is configured to emit a homogenous illumination profile to illuminate the skin region of the subject homogenously. According to said aspect, an optical diffuser which may selectively be arranged inside or outside the path of light is not needed anymore.

A problem that typically arises is that secondary illumination 'pollutes' the measured PPG or SC signals. Secondary illumination is light that is reflected or remitted from the tissue and then reflected off a non-tissue object to illuminate the tissue a second time. In order to suppress this secondary selection, the system 500' may comprise highly absorbing baffles 350 that are coated to absorb remitted light to avoid secondary illumination. These baffles 350 may be arranged such that the measured SC or PPG signals are not polluted by the secondary illumination. Alternatively or additionally, the system 500″ may also comprise polarizers 410, 420 to minimize the secondary illumination.

Figure 12:
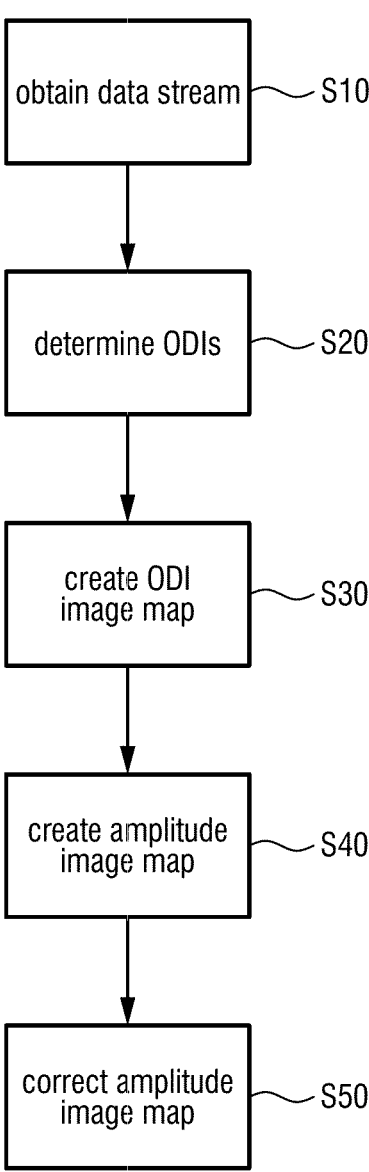
FIG. 12 shows a flowchart illustrating a method to be executed by the device for providing imaging of one or more aspects of blood perfusion induced by cardiac induced blood motion in a skin region according to the present invention.

FIG. 12 shows a flowchart illustrating a method to be executed by the device 100 for providing imaging of one or more aspects of blood perfusion induced by cardiac induced blood motion in a skin region according to the present invention. The device 100 comprises a processing unit 110 which is configured to execute steps S10-S50 as shown in FIG. 12. It is clear that this processing unit is not configured to image the one or more aspects of blood perfusion, but this processing unit is configured to provide the imaging by performing all processing steps before imaging the one or more aspects. The processing unit 110 may, e.g., be a processor of a computer and may thus be configured to execute all steps S10-S50 such that a display unit connected to the processing unit is configured to image the one or more aspects.

In a first step S10, the processing unit obtains data streams. The data streams are derived from detected electromagnetic radiation transmitted through or reflected from the skin region to be investigated. Further, said data streams comprise a data signal per skin pixel for a plurality of skin pixels of the skin region. A first data stream is derived from a patterned illumination of the skin region and a second data stream is derived from a patterned illumination and/or homogenous illumination of the skin region. Hence, in other words, the first data stream is derived from the radial imaging and the second data stream is derived from the widefield imaging.

In step S20, the processing unit determines, per skin pixel or group of skin pixels, from the data signals of the first data stream and the second data stream, optical depth indices, ODIs. This determination of the ODIs is done by dividing, per skin pixel or group of skin pixels, data signals of the first data stream by data signals of the second data stream, wherein the ODIs are indicative of the depth of the blood flow within the skin region at the skin pixels or groups of skin pixels.

In step S30, an ODI image map of the skin region including the plurality of skin pixels is created from the determined ODIs.

In step S40, an amplitude image map of the skin region including the plurality of skin pixels is created from the data signals of the second data stream.

Last but not least, in the last step S50, the amplitude image map is corrected by correcting, per skin pixel or group of skin pixels, the data signals of the second data stream by the determined ODIs.

Figure 13:
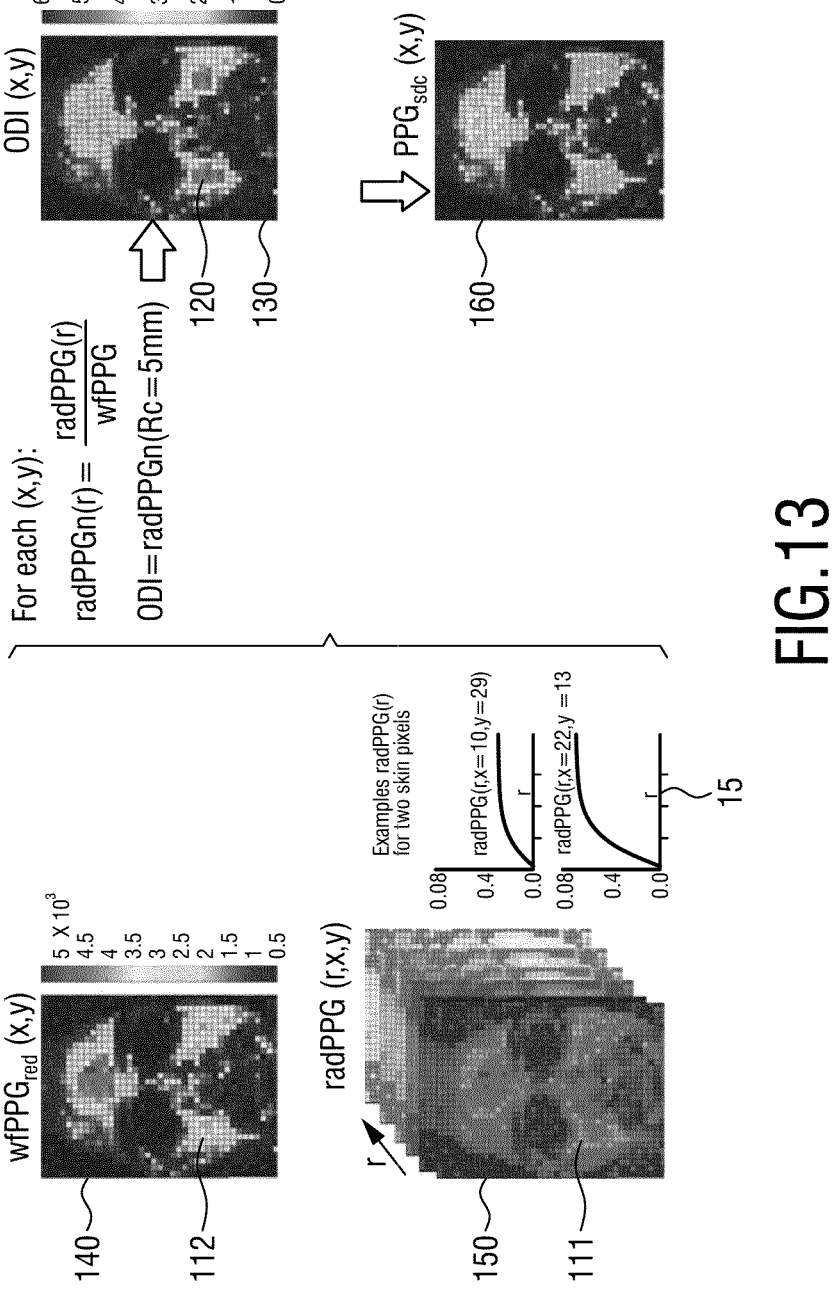
FIG. 13 shows a schematic diagram which visualizes the processing steps S20-S50 of the method as shown in FIG. 12.

FIG. 13 shows a schematic diagram which visualizes the processing steps S20-S50 of the method as shown in FIG. 12. A widefield PPG image map wfPPG(x,y) 140 and radial PPG image maps radPPG (r,x,y) 150 are shown on the left of FIG. 13. The widefield PPG image map 140 is also called 'amplitude image map' 140 in the following. The amplitude image map 140 is preferably created from data signals 112 of the second data stream which is derived from a homogenous illumination of the skin region (i.e., from widefield imaging). Hence, this amplitude image map 140 is a conventional PPG image map as known in the art (cf. also Verkruysse et al.: "Remote plethysmographic imaging using ambient light", 2008). Accordingly, the amplitude image map 140 being a false color map as shown in FIG. 13 reflects the amplitude of the data signals of the second data stream for each skin pixel our group of skin pixels. In case of PPG, the false color may reflect the ratio AC/DC obtained from widefield PPG imaging. In case of SC, the false color may either reflect the pulsatile component of the perfusion signal or the constant component of the perfusion signal obtained from widefield SC imaging.

The radial PPG image maps radPPG (r,x,y) 150 are not necessarily required for the present invention, but may additionally be created from data signals 111 of the first data stream which is derived from a patterned illumination (i.e., from radial imaging). In case of PPG, the false color may reflect the ratio AC/DC obtained from radial PPG imaging. In case of SC, the false color may either reflect the pulsatile component of the perfusion signal or the constant component of the perfusion signal obtained from radial SC imaging.

An ODI image map ODI (x, y) 130 is shown on the right of FIG. 13. This ODI image map 130 is created from ODIs 120 which are determined before. These ODIs are determined by dividing, per skin pixel or group of skin pixels, data signals 111 of the first data stream by data signals 112 of the second stream, i.e., the ODI image map 130 as shown in FIG. 13 may be created from combining the amplitude image map 140 (wfPPG (x,y) in FIG. 13) and the radial image maps 150.

Preferably, for each skin pixel or group of skin pixels with coordinates (x,y) an ODI is determined by determining the ratio radPPGn(r)=radPPG(r)/wfPPG (in case of PPG measurements) or the ratio radSCn(r)=radSC(r)/wfSC (in case of SC measurements). Exemplarily, FIG. 13 shows how the ODIs are determined for PPG measurements. To create the ODI image map 130, multiple skin pixels are illuminated either sequentially or simultaneously (but at sufficient distance from one another). This allows creating ODIs 120 for different spatial tissue locations and thus forming the ODI image map 130 as shown in FIG. 13.

In case of SC measurements, the pulsatile components or the constant components of the measured perfusion signal are used to calculate a map $ODI_{puls}$ is (x,y) which indicates the depth of the pulsatile flow in vessels (arterioles likely) or a map $ODI_{const}$ (x,y) which indicates the depth of the averaged, non-pulsatile flow in all vessels with blood flow (both maps not shown in FIG. 13).

The ODI image map 130 as shown in FIG. 13 illustrates that the ODI on the forehead is small while the ODI on the cheeks of the subject is large. This illustrates that the PPG or SC signals measured on the forehead result from shallow vessels while the PPG or SC signals measured on the cheeks result from deeper vessels. In general, the ODIs are indicative of the depth of blood flow within the skin region at the skin pixels or groups of skin pixels.

As further shown in FIG. 13 for PPG, the ODIs may be determined, per skin pixel or group of skin pixels, by selecting values of the ratios of the time-varying AC components and the constant DC components of the data signals 111 of the first data stream (i.e., by selecting values of the radPPG(r) curve) at predetermined radial distances 15 between the skin pixels or groups of skin pixels and illumination spots of the patterned illumination. Exemplarily, FIG. 13 shows that a predetermined radial distance 15 of 5 mm is used to select the value of the ratio AC/DC (radPPG (r=Rc=5 mm)) of the data signals 111 of the first data stream for each skin pixel (x,y).

In the last step S50, the amplitude image map 140 is corrected for depth. This is done by correcting, per skin pixel or group of skin pixels, the data signals 112 of the amplitude image map 140 by the determined ODIs 120 of the determined ODI image map 130. Accordingly, a source depth corrected amplitude image map $PPG_{sdc}$ (x,y) 160 is obtained in the end. More details about this last correction step can be found in subsequent FIG. 14.

Figure 14:
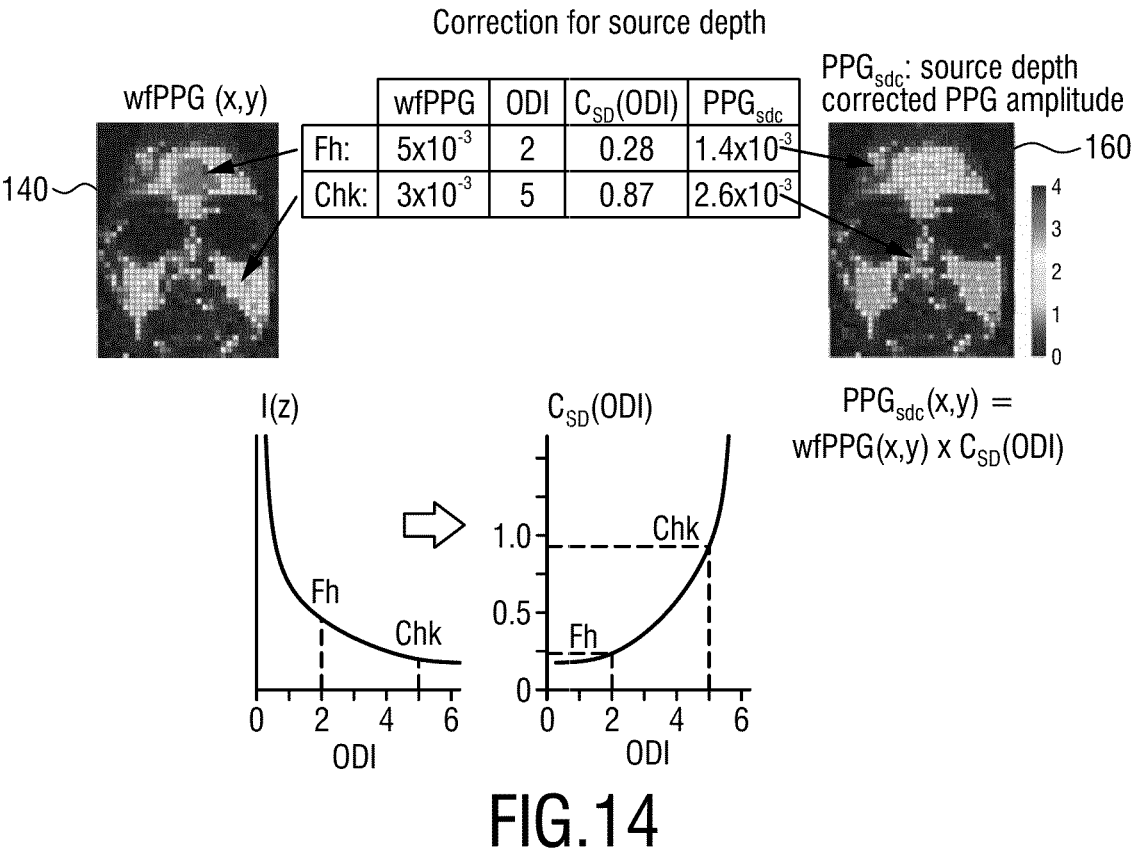
FIG. 14 shows a schematic diagram which visualizes the processing step S50 of the method as shown in FIG. 12.

FIG. 14 shows a schematic diagram which visualizes the processing step S50 of the method as shown in FIG. 12. The source depth corrected amplitude image map $PPG_{sdc}$ (x,y) 160 is obtained by correcting the amplitude image map 140 for depth. The equation $PPG_{sdc}$ (x,y)=wfPPG(x,y)×$C_{sd}$ (ODI) expresses that per skin pixel or group of skin pixels the data signals 112 of the amplitude image map 140 are corrected by a correction factor $C_{sd}$(ODI) which depends on the determined ODIs. This means that on the forehead and on the cheek different correction factors $C_{sd}$(ODI) ($C_{sd}$=0.28 for ODI=2 on the forehead and $C_{sd}$=0.87 for ODI=5 on the cheek) are used to correct the data signals 112 of the amplitude image map 140. This is because the ODI on the forehead is small (ODI=2) and the ODI on the cheeks is large (ODI=5). In other words, the amplitude image map 140 is corrected by correcting, per skin pixel or group of skin pixels, the data signals 112 of the second data stream by the determined ODIs.

Figure 15:
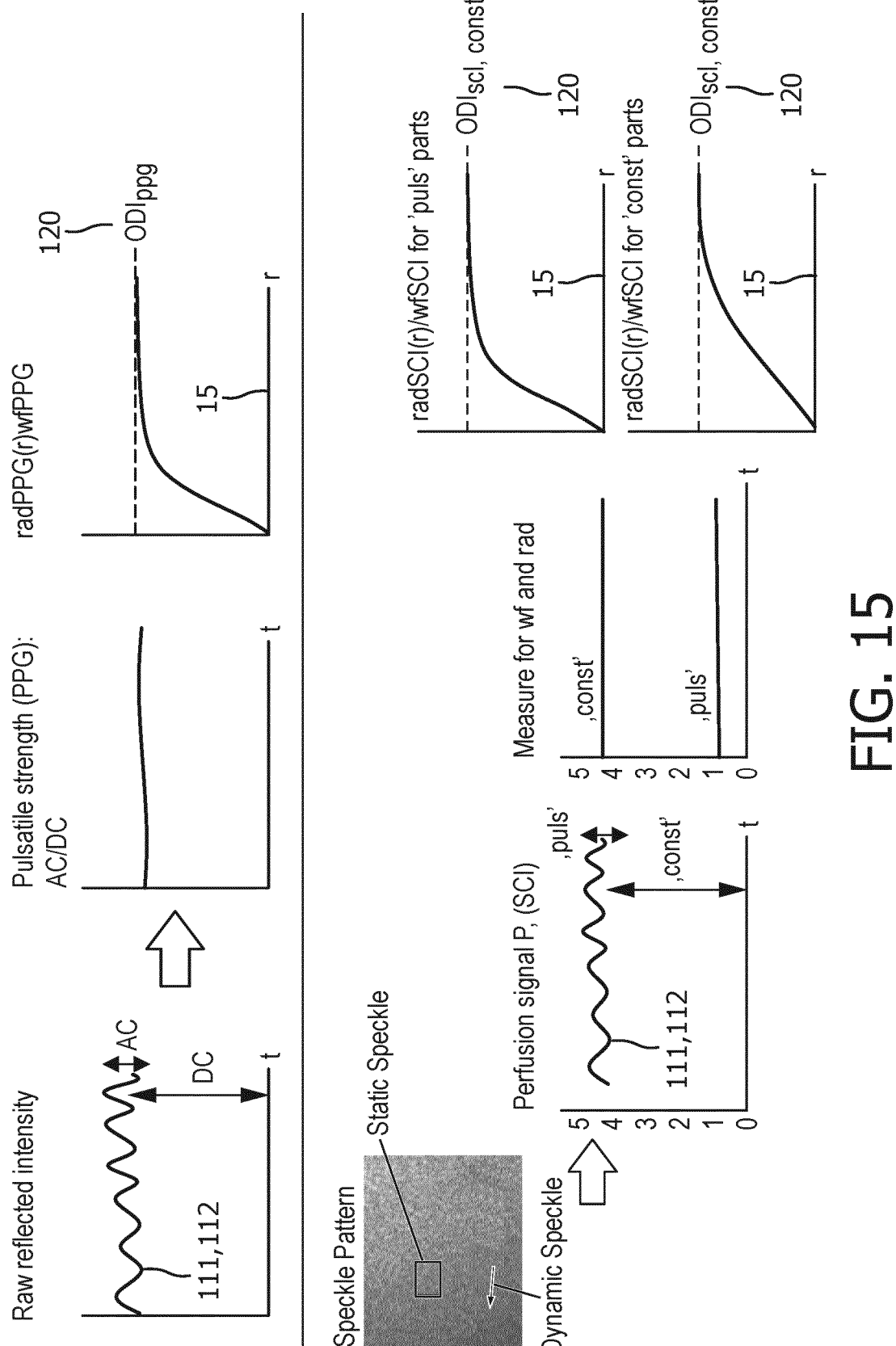
FIG. 15 shows a schematic diagram which illustrates the analogy and differences between SC and PPG.

FIG. 15 shows a schematic diagram which illustrates the analogy and differences between SC and PPG. For PPG, the pulsatile strength AC/DC is preferably calculated from the raw reflected intensity signal for both widefield PPG and radial PPG to obtain a wfPPG signal and a radPPG(r) signal. Further, in case PPG, the $ODI_{PPG}$ 120 is preferably calculated by determining the ratio of these signals. Hence, in case of PPG, the data signals 111, 112 of the first and second data stream (as illustrated in FIG. 13) are raw intensity signals.

For SC, the data signals 111, 112 of the first and second data stream are preferably perfusion signals that are split into pulsatile components which represent the cardiac induced pulsatile blood motion in vessels of the skin region and a constant component which represents the averaged non-pulsatile blood motion in vessels of the skin region. The $ODI_{sci,puls}$, $ODI_{sci,const}$ 120 is calculated by either determining the ratio of radSCI(r) and wfSCI for the pulsatile component ('puls') or by determining said ratio for the constant component ('const'). That also means that different ODI image maps 130 as shown in FIG. 13 are preferably created for the pulsatile or the constant component of the perfusion signal. Further, also the amplitude image map $wfPPG_{red}$ (x,y) 140 and the radial image map radPPG (r,x,y) 150 as illustrated in FIG. 13 are either created from the pulsatile components or the constant components of the perfusion signals. Further, it shall be mentioned that for SC, the ODIs may be determined, per skin pixel or group of skin pixels, by selecting values of the pulsatile or constant components of the data signals of the first data stream at predetermined radial distances 15 between the skin pixels or groups of skin pixels and illumination spots of the patterned illumination. Exemplarily, said predetermined radial distance r 15 is quite large in FIG. 15, where the curve radSCI(r)/wfSCI goes over into a plateau.

The process of how to obtain a perfusion signal from a raw speckle pattern for SCI is illustrated in FIG. 4. Further details can also be found in subsequent FIG. 16.

Figure 16:
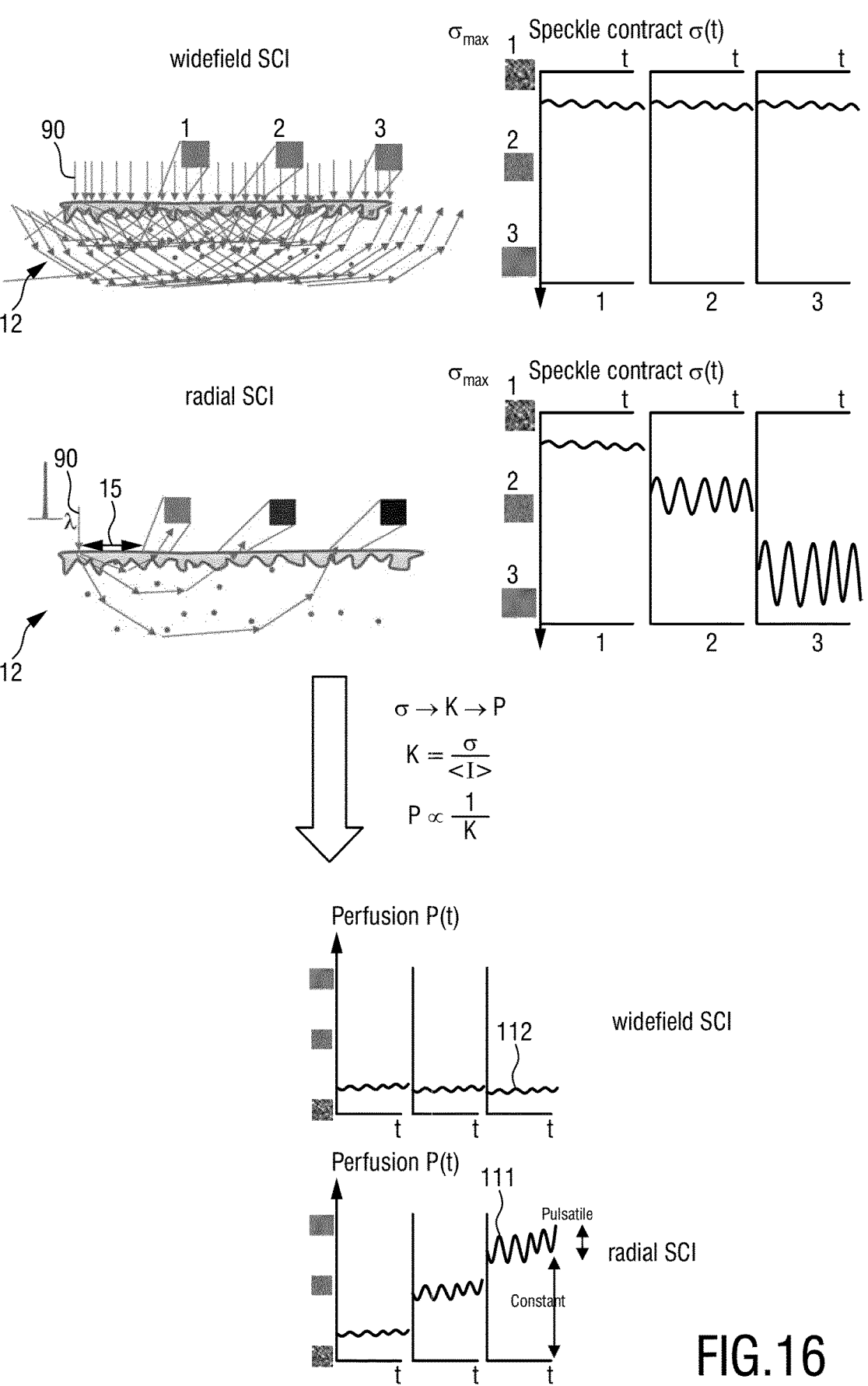
FIG. 16 shows a schematic diagram which illustrates contrast signals and their translation into perfusion signals for widefield SC imaging and radial SC imaging.

FIG. 16 shows a schematic diagram which illustrates contrast signals and their translation into perfusion signals for widefield SCI and radial SCI. In widefield SCI imaging, where the skin region 12 is illuminated with coherent light homogenously (in difference to PPG where coherent or incoherent light can be used) or by a pattern, the contrast a is high and time-modulated due to pulsatile flow. In radial SCI imaging, where the skin region 12 is illuminated with one coherent pencil beam (or a pattern of coherent pencil beams), the contrast is smaller for larger radial distances 15 from the laser spot. The time-modulated part (from pulsatile flow) is larger as well as the overall flow. Essentially, for radial SCI the same principles are used as for radial PPGI: the longer the light has travelled through the tissue, the more it has picked up the relevant signal from that tissue (cf. also FIGS. 6A and 6B). In PPG, said signal is simple the modulation depth of the intensity (resulting from volume pulsatile vessels). In SCI, said signal is the reduced speckle contrast due to flow.

It shall be noted that although the primary signals for PPG and SCI appear very similar, there is an important difference. In PPG, the normalization for the AC part with the DC part makes sense since the primary signals of the first and second data stream are light intensities and the normalization cancels out the light intensities as both AC and DC are proportional to it. Accordingly, the modulation depths after normalization are preferably the data signals to consider further. In SCI, the primary signals (i.e., the data signals of the first and second data stream) are preferably perfusion signals P(t) (cf. FIG. 16) and a normalization as in PPG does not make sense. Rather, the pulsatile components and the constant components are processed as separate independent components.

Figure 17:
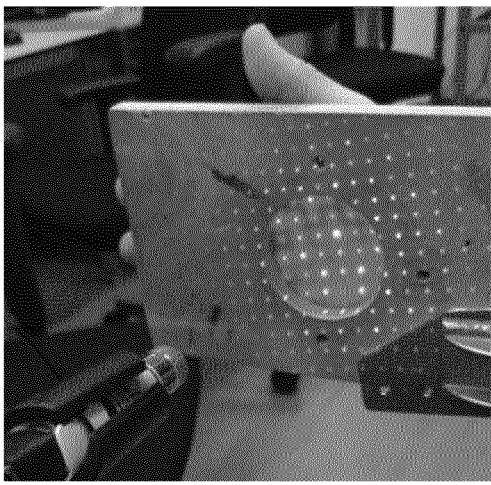
FIG. 17 shows pictures with different illumination patterns used for the patterned illumination according to the present invention.
Figure 17:
Figure 17:
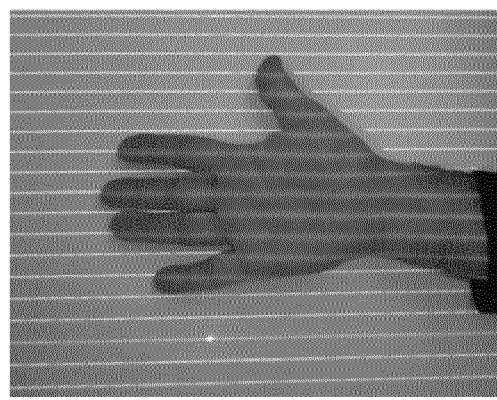
Figure 18:
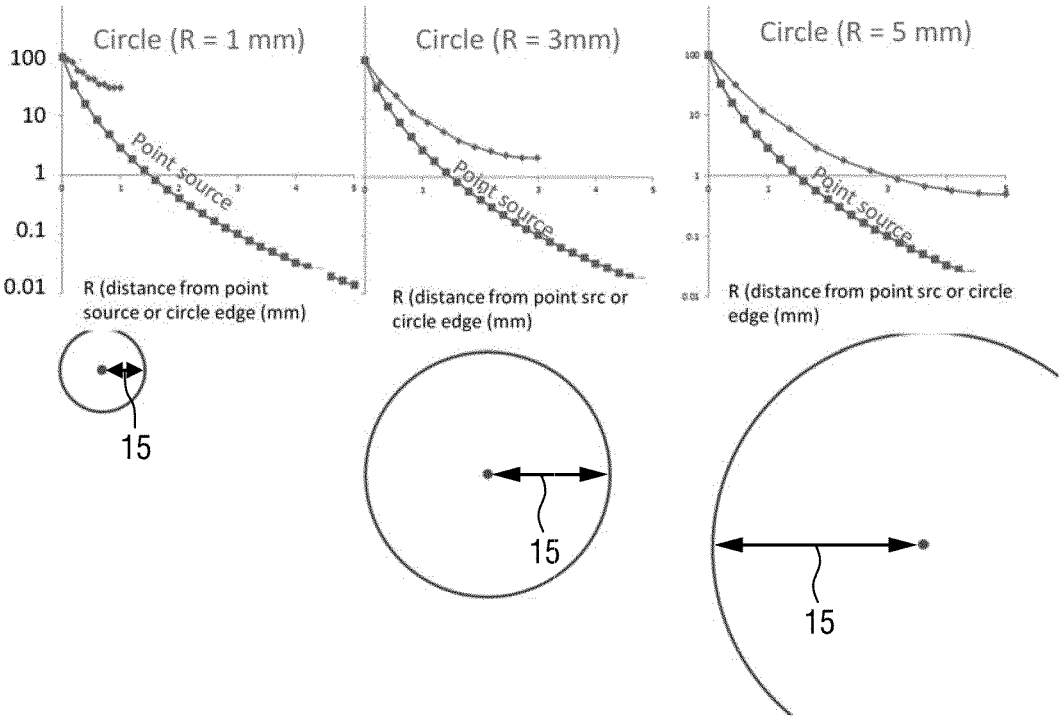
FIG. 18 which shows a schematic diagram with an analytical comparison between a point source illumination and a circular illumination.

FIG. 17 shows pictures with different illumination patterns used for the patterned illumination according to the present invention. The illumination used for radial PPG and radial SC measurements has so far been mainly discussed with one pencil beam, such as one single laser spot on the skin of the subject. FIG. 17 illustrates that various different illumination patterns, such as patterns of dots, circles or stripes may be used. Circles or rings and lines have the advantage that the DC levels of the measured signals decrease less drastic with radial distance 15 than with a pencil beam and may thus be less demanding on the dynamic range of the detector (e.g. camera). For a circle, the radial dependence of the AC/DC (which contains the ODI information for PPG) is similar while the dynamic range (DC) is more advantageous. Similar arguments can be made for line illuminations or other types of structural illumination. This is also illustrated in subsequent FIG. 18 which shows an analytical comparison between a point source illumination and a circular illumination. While a more beneficial DC range is gained with a circular illumination, price is paid in the sense that the range of radial distance 15 is now limited. For line illuminations, or other types of structural illumination, similar compromises exist.

Figure 19:
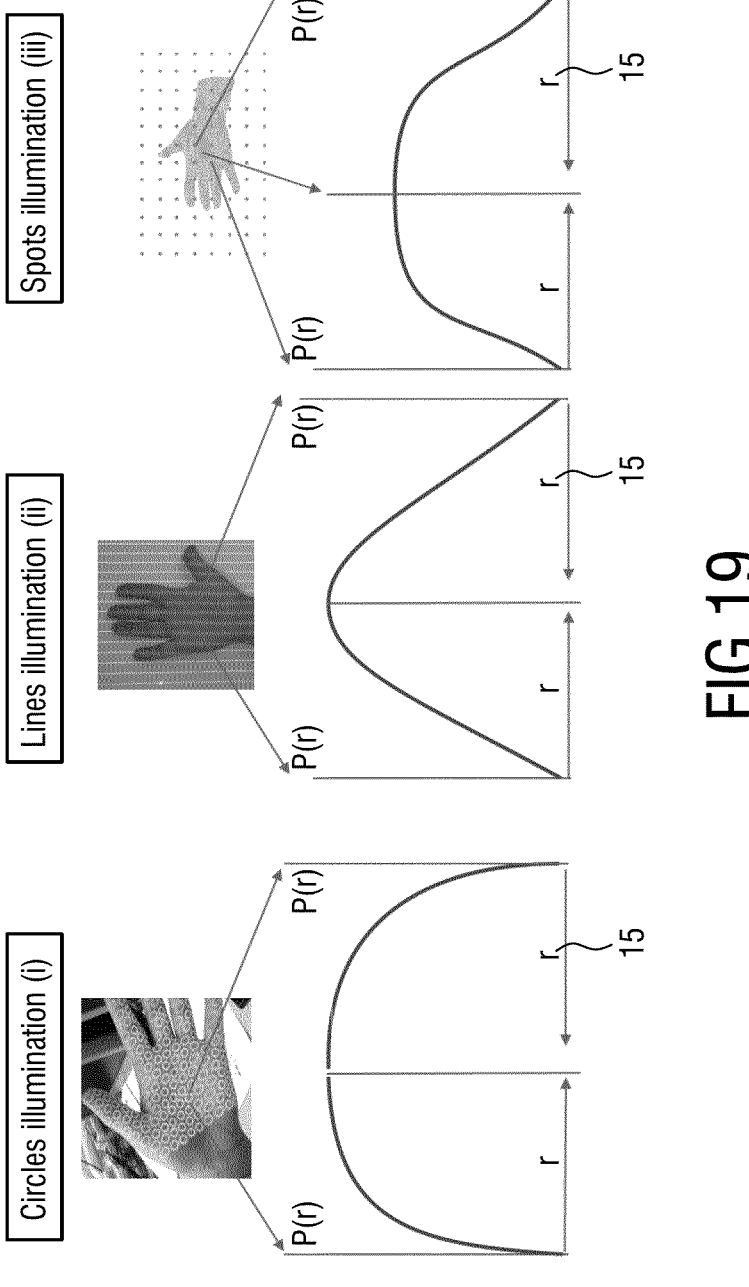
FIG. 19 shows a schematic diagram which illustrates different types of illumination and the point at which to select the value for ODI determination less arbitrary.

FIG. 19 shows a schematic diagram which illustrates different types of illumination and the point at which to select the value for ODI determination less arbitrary. The different types of illumination as shown in FIG. 19 can exemplarily be split into circles illumination (i), lines illumination (ii) and spots illumination (iii).

For circles illumination (i), the center of the illumination circles is preferably chosen to determine the ODI.

For lines illumination (ii), a predefined distance between illumination lines or the center between two illumination lines is preferably chosen to determine the ODI.

For spots or multiple point illumination (iii) either the point with the maximum perfusion signal $P_{max}$(r) or the point in between two illumination spots is preferably chosen to determine the ODI.

Further, in order to make higher resolution image maps from the rather coarse resolution points, several techniques are proposed which are explained in the following with reference to FIG. 20. These techniques include interpolation, translation, rotation and combinations of these.

Figure 20:
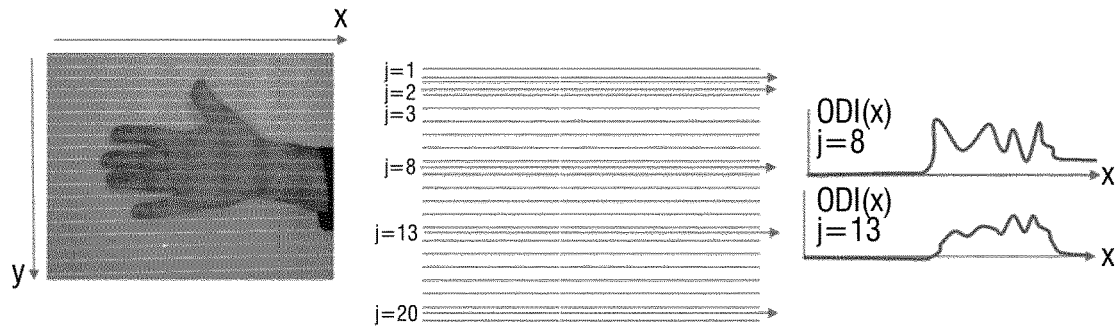
FIG. 20 shows a schematic diagram which illustrates several embodiments (options 1-6) to improve the resolution of the ODI and source depth corrected images.
Figure 20:
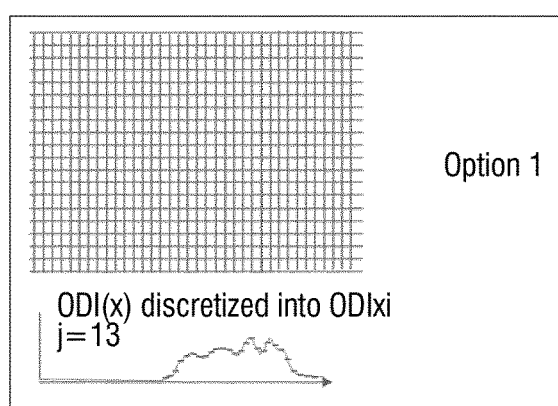
Figure 20:
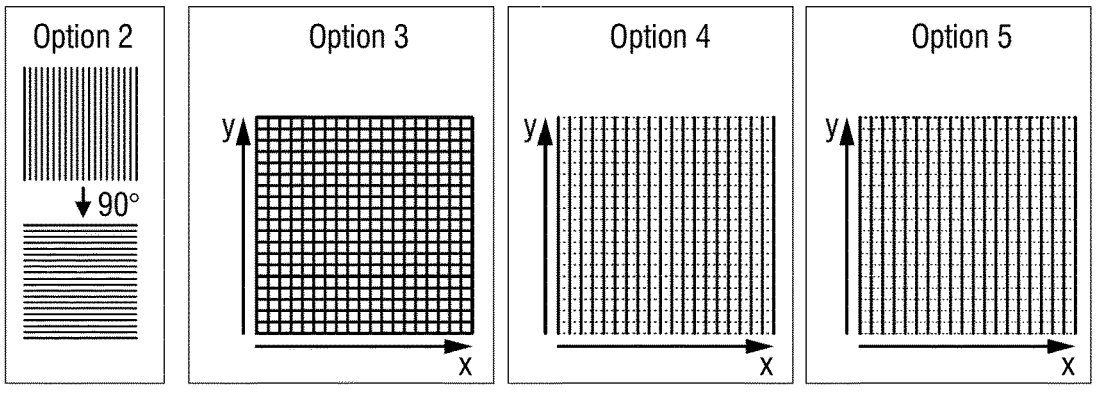
Figure 20:
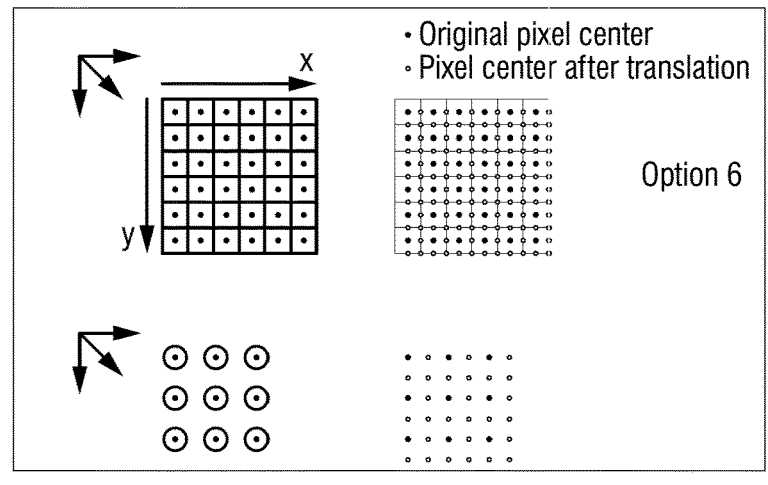

FIG. 20 shows a schematic diagram which illustrates several embodiments (Options 1-6) to improve the resolution of the ODI and source depth corrected images. As shown on the top of FIG. 20, it is possible to obtain 20 ODI(x) curves from an illumination pattern with 21 lines as for each $y_j$ ODI(x) is determined. Option 1 comprises the step of discretizing line measurements to make pixels. Hence, for each line j, the ODI(x) curve is discretized into $ODI_{xj}$. Then, for each skin pixel or each group of skin pixels i, j the ODI image map is created from the discretized ODIs in order to correct the perfusion signals for depth.

Another option 2 comprises first obtaining $ODI_{xj}$ data with lines illumination, then rotate the illumination pattern by 90° to obtain $ODI_{yj}$ data. Then determine $ODI_{ij}$ as the average of the $ODI_{xj}$ and $ODI_{yj}$ data and proceed with creating ODI image maps from the determined $ODI_{ij}$.

For option 3, illumination is performed with a grid and the ODI for skin pixel i,j is chosen as the value in the center of each skin pixel or group of skin pixels. With respect to option 2, this option 3 provides the advantage that it is faster.

For option 4, illumination is performed simultaneously with two orthogonal sets of lines L1 and L2, with wavelengths λ1 and λ2, respectively. Two illumination units, such as two cameras, equipped with bandpass filters to pass the wavelengths λ1 and λ2 record each line pattern independently since the passbands do not overlap. Wavelengths λ1 and λ2 are chosen such that they are very close to ensure that optical properties of the tissue are very similar, small enough to not affect the penetration depths appreciably. The bandpass filters have very small passbands for this purpose. Choosing wavelengths for which optical properties (absorption and scattering) are very similar is possible by choosing them in a region where blood (dominant chromophore) does not change appreciably (e.g., in the range around 660 nm).

For option 5, illumination is performed simultaneously with two orthogonal sets of lines of the same wavelength, but the pattern and their recordings at the imaging unit(s) are time multiplexed (either time modulated or frequency modulated).

For the last option 6, the illumination is performed with a grid with considerable square sizes (e.g., 5×5 mm) to ensure that light at the center of the squares has travelled considerable depth/distance. To mitigate the low image resolution that would result from this coarser grid, the illumination is also performed at translations of this grid and the coarse resolution images are combined into one image of higher resolution. Preferably, four illuminations/recordings are done simultaneously using the wavelength choices of option 4, or time multiplexed as proposed in option 5. In FIG. 20, three translations of the grid are indicated by three arrows, for translations, e.g., over 0.5 grid periods, resulting in doubling the resolution in both x and y directions. Obviously, 9 illuminations translated over 0.333 periods give an even higher effective image resolution, at the cost of having to multiplex more. Further, such translations are not only possible for illumination grids but also for circles or points as shown for option 6 in FIG. 20.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Device for providing imaging of one or more aspects of blood perfusion induced by cardiac induced blood motion in a skin region of a subject, said device comprising a processing unit configured to:

obtain data streams derived from detected electromagnetic radiation transmitted through or reflected from the skin region, said data streams comprising a data signal per skin pixel for a plurality of skin pixels of the skin region, wherein a first data stream is derived from radial imaging of the skin region and a second data stream is derived from widefield imaging the skin region, wherein both the first data stream and the second data stream are acquired at substantially the same wavelength;

determine, per skin pixel or group of skin pixels, from the data signals of the first data stream and the second data stream, optical depth indices, ODIs, by dividing, per skin pixel or group of skin pixels, data signals of the first data stream by data signals of the second data stream, wherein the ODIs are indicative of the depth of the blood flow within the skin region at the skin pixels or groups of skin pixels;

create an ODI image map of the skin region including the plurality of skin pixels from the determined ODIs;

create an amplitude image map of the skin region including the plurality of skin pixels from amplitudes of the data signals of the second data stream; and correct the amplitude image map by correcting, per skin pixel or group of skin pixels, the amplitudes of the data signals of the second data stream by the determined ODIs.

2. Device according to claim 1, wherein the processing unit is configured to correct the amplitude image map by estimating source depths of the blood flow within the skin region at the skin pixels or groups of skin pixels from the determined ODIs and by correcting, per skin pixel or group of skin pixels, the amplitudes of the data signals of the second data stream by the estimated source depths of the blood flow.

3. Device according to claim 2, wherein the amplitudes of the data signals of the second data stream are proportional to exp $(-2\mu_a SD)$, where $\mu_a$ is a predetermined tissue attenuation coefficient and SD is the estimated source depth of the blood motion within the skin region at a skin pixel or a group of skin pixels.

4. Device according to claim 1, wherein the processing unit is configured to derive, in case of a patterned illumination, the data signals of the second data stream by a spatial integral of the electromagnetic radiation transmitted through or reflected from the skin region.

5. Device according to claim 1, wherein the data signals of the first and second data stream comprise time-varying AC components and constant DC components, and wherein the processing unit is configured to create the amplitude image map by determining, per skin pixel or group of skin pixels, ratios of the time-varying AC components and the constant DC components of the data signals of the second data stream.

6. Device according to claim 5, wherein the processing unit is configured to determine, per skin pixel or group of skin pixels, the ODIs from the data signals of the first and second data stream by dividing, per skin pixel or group of skin pixels, ratios of the time-varying AC components and the constant DC components of the data signals of the first data stream by ratios of the time-varying AC components and the constant DC components of the data signals of the second data stream.

7. Device according to claim 6, wherein the processing unit is further configured to determine, per skin pixel or group of skin pixels, the ODIs by selecting values of the ratios of the time-varying AC components and the constant DC components of the data signals of the first data stream at predetermined radial distances between the skin pixels or groups of skin pixels and illumination spots of the patterned illumination.

8. Device according to claim 1, wherein the data signals of the first and second data stream comprise pulsatile components and/or constant components, the pulsatile components representing the cardiac induced pulsatile blood motion in vessels of the skin region and the constant components representing the averaged non-pulsatile blood motion in vessels of the skin region, and wherein the processing unit is configured to create the amplitude image map from the pulsatile or constant components of the data signals of the second data stream.

9. Device according to claim 8, wherein the processing unit is configured to determine, per skin pixel or group of skin pixels, the ODIs from the data signals of the first and second data stream by
  i) dividing, per skin pixel or group of skin pixels, the pulsatile components of the data signals of the first data stream by the pulsatile components of the data signals of the second data stream, or
  ii) dividing, per skin pixel or group of skin pixels, the constant components of the data signals of the first data stream by the constant components of the data signals of the second data stream.

10. Device according to claim 9, wherein the processing unit is further configured to determine, per skin pixel or group of skin pixels, the ODIs by selecting values of the pulsatile or constant components of the data signals of the first data stream at predetermined radial distances between the skin pixels or groups of skin pixels and illumination spots of the patterned illumination.

11. System for providing imaging of one or more aspects of blood perfusion induced by cardiac induced blood motion in a skin region of a subject, said system comprising:
  a first illumination unit configured to emit a pattern of electromagnetic radiation to illuminate the skin region of the subject by a patterned illumination for radial imaging;
  a second illumination unit configured to emit a homogenous illumination profile to illuminate the skin region of the subject homogenously for widefield imaging;

an imaging unit configured to detect the electromagnetic radiation transmitted through or reflected from the skin region of the subject and to derive data streams from the detected electromagnetic radiation; and
  a device for providing imaging of one or more aspects of blood perfusion induced by cardiac induced blood motion in a skin region of a subject according to claim 1 from the obtained data streams, wherein the device is configured to obtain a first data stream derived from a radial imaging of the skin region and a second data stream derived from a widefield imaging of the skin region, wherein both the first data stream and the second data stream are acquired at substantially the same wavelength.

12. System for providing imaging of one or more aspects of blood perfusion induced by cardiac induced blood motion in a skin region of a subject, said system comprising:
  an illumination unit configured to emit a narrow radiation beam of electromagnetic radiation;
  an optical diffuser configured to diffuse the electromagnetic radiation emitted by the illumination unit to illuminate the skin region of the subject homogenously and/or by a patterned illumination either by a patterned illumination for radial imaging or by a homogenous illumination for widefield imaging;
  an imaging unit configured to detect the electromagnetic radiation transmitted through or reflected from the skin region of the subject and to derive data streams from the detected electromagnetic radiation; and
  a device for providing imaging of one or more aspects of blood perfusion induced by cardiac induced blood motion in a skin region of a subject according to any one of the preceding claims from the obtained data streams, wherein the device is configured to obtain a first data stream derived from a radial imaging of the skin region and a second data stream derived from a widefield imaging of the skin region, wherein both the first data stream and the second data stream are acquired at substantially the same wavelength.

13. System according to claim 12,
  wherein the imaging unit comprises an optical sensing array, in particular a two-dimensional image sensor, including a filter providing at least two different wavelength channels, and
  the illumination unit is configured to emit electromagnetic radiation for illuminating the skin region of the subject with light in said at least two different wavelength channels.

14. Method for providing imaging of one or more aspects of blood perfusion induced by cardiac induced blood motion in a skin region of a subject, said method comprising the steps of:
  obtaining data streams derived from detected electromagnetic radiation transmitted through or reflected from the skin region, said data streams comprising a data signal per skin pixel for a plurality of skin pixels of the skin region, wherein a first data stream is derived from radial imaging of the skin region and a second data stream is derived from widefield imaging of the skin region, wherein both the first data stream and the second data stream are acquired at substantially the same wavelength;
  determining, per skin pixel or group of skin pixels, from the data signals of the first data stream and the second data stream, optical depth indices, ODIs, by dividing, per skin pixel or group of skin pixels, data signals of the first data stream by data signals of the second data stream, wherein the ODIs are indicative of the depth of the blood flow within the skin region at the skin pixels or groups of skin pixels;

creating an ODI image map of the skin region including the plurality of skin pixels from the determined ODIs;

creating an amplitude image map of the skin region including the plurality of skin pixels from amplitudes of the data signals of the second data stream; and correcting the amplitude image map by correcting, per skin pixel or group of skin pixels, the amplitudes of the data signals of the second data stream by the determined ODIs.

15. Computer program comprising program code means for causing a computer to carry out the steps of the method as claimed in claim 14 when said computer program is carried out on a computer.

* * * * *